(12) United States Patent
Zmuda et al.

(10) Patent No.: US 9,181,345 B2
(45) Date of Patent: Nov. 10, 2015

(54) METHODS OF TREATING LUPUS

(75) Inventors: Jonathan Zmuda, Frederick, MD (US);
Christina Strange, Frederick, MD (US);
Wendy Irene White, Germantown, MD (US)

(73) Assignee: MEDIMMUNE, LLC, Gaithersburg, MD (US)

( * ) Notice: Subject to any disclaimer, the term of this patent is extended or adjusted under 35 U.S.C. 154(b) by 245 days.

(21) Appl. No.: 13/290,850

(22) Filed: Nov. 7, 2011

(65) Prior Publication Data

US 2012/0219555 A1 Aug. 30, 2012

Related U.S. Application Data

(63) Continuation of application No. 12/598,524, filed as application No. PCT/US2008/062639 on May 5, 2008, now abandoned, which is a continuation of application No. PCT/US2007/024947, filed on Dec. 6, 2007, which is a continuation-in-part of application No. PCT/US2007/024941, filed on Dec. 6, 2007.

(60) Provisional application No. 60/924,219, filed on May 3, 2007, provisional application No. 60/924,220, filed on May 3, 2007, provisional application No. 60/924,584, filed on May 21, 2007, provisional application No. 60/960,187, filed on Sep. 19, 2007, provisional application No. 60/996,174, filed on Nov. 5, 2007, provisional application No. 60/996,176, filed on Nov. 5, 2007, provisional application No. 60/996,219, filed on Nov. 6, 2007, provisional application No. 60/996,820, filed on Dec. 6, 2007, provisional application No. 61/006,963, filed on Feb. 8, 2008.

(51) Int. Cl.
| | |
|---|---|
| *A61K 39/395* | (2006.01) |
| *A61K 38/21* | (2006.01) |
| *C07K 16/24* | (2006.01) |
| *C07K 14/56* | (2006.01) |
| *G01N 33/564* | (2006.01) |
| *C07K 16/28* | (2006.01) |
| *C07K 16/42* | (2006.01) |
| *C12Q 1/68* | (2006.01) |
| *A61K 39/00* | (2006.01) |

(52) U.S. Cl.
CPC ............. *C07K 16/2866* (2013.01); *A61K 38/21* (2013.01); *A61K 39/3955* (2013.01); *C07K 16/241* (2013.01); *C07K 16/4241* (2013.01); *C12Q 1/6883* (2013.01); *G01N 33/564* (2013.01); *A61K 2039/505* (2013.01); *C07K 14/56* (2013.01); *C12Q 2600/158* (2013.01); *G01N 2333/56* (2013.01); *G01N 2333/70567* (2013.01); *G01N 2800/104* (2013.01); *G01N 2800/205* (2013.01); *G01N 2800/52* (2013.01)

(58) Field of Classification Search
CPC ........... A61K 39/395; A61K 2039/505; A61K 38/21; C07K 16/249; C12Q 2600/158; G01N 33/564; G01N 2333/56; G01N 2800/104; G01N 2333/70567; G01N 2800/52
See application file for complete search history.

(56) References Cited

U.S. PATENT DOCUMENTS

| | | | |
|---|---|---|---|
| 5,888,511 A | 3/1999 | Skurkovich et al. | |
| 6,333,032 B1 | 12/2001 | Skurkovich et al. | |
| 2004/0067232 A1* | 4/2004 | Banchereau et al. | 424/145.1 |
| 2005/0261215 A1 | 11/2005 | Garren et al. | |
| 2007/0014724 A1* | 1/2007 | Witte et al. | 424/1.49 |
| 2007/0092890 A1 | 4/2007 | Abbas | |
| 2007/0117105 A1* | 5/2007 | Crow et al. | 435/6 |
| 2010/0143372 A1* | 6/2010 | Yao et al. | 424/158.1 |
| 2011/0287022 A1* | 11/2011 | Yao et al. | 424/158.1 |

FOREIGN PATENT DOCUMENTS

| | | |
|---|---|---|
| WO | 02/066649 A2 | 8/2002 |
| WO | 2005/059106 A2 | 6/2005 |
| WO | 2005/103300 A2 | 11/2005 |

OTHER PUBLICATIONS

Backing, Christian, "MedImmune Expands Anti-Interferon-Alpha Program by Initiating Phase 1 Trial in Patients With Psoriasis," Medical News Today, MediLexicon, Intl, (Mar. 2007).
Bissonnette et al., "A randdomized, double-blind, placebo-controlled, phase I study of MEDI-545, an anti-interferon-alfa monoclonal antibody, in subjects with chronic psoriasis," J. Acad. Dermatol. 62:427-436 (Mar. 2010).
Franceschini, et al., "Anti-Ro/SSA and La/SSB antbodies," Autoimmunity, 38(1):55-63 (Feb. 2005).
Fujita, et al., "Enzyme-linked immunosorbent assay for anti-tropomyosin antbodies and its clinical application to various heart diseases," J. Clinica Chimica Acta, 299:179-92 (2000).
Matsushita et al., "Autoimmune Response to Proteasome Activator 28-Alpha in Patients with Connective Tissue Diseases," J. Rheumatology, 31(2):252-59 (2004).
International Search Report mailed on Oct. 14, 2008. In connection with corresponding International Application No. PCT/US08/62639.
Supplementary Partial European Search Report mailed on Apr. 28, 2011, in connection with corresponding European Patent Application No. EP08769294.

\* cited by examiner

*Primary Examiner* — Robert Landsman
*Assistant Examiner* — Bruce D Hissong

(57) ABSTRACT

The present invention encompasses auto-antibodies associated with autoimmune disorders. The auto-antibodies may be used, for example, in methods of treating patients, methods of diagnosing patients, methods of monitoring disease progression of patients, and methods of prognosing patients.

15 Claims, 12 Drawing Sheets

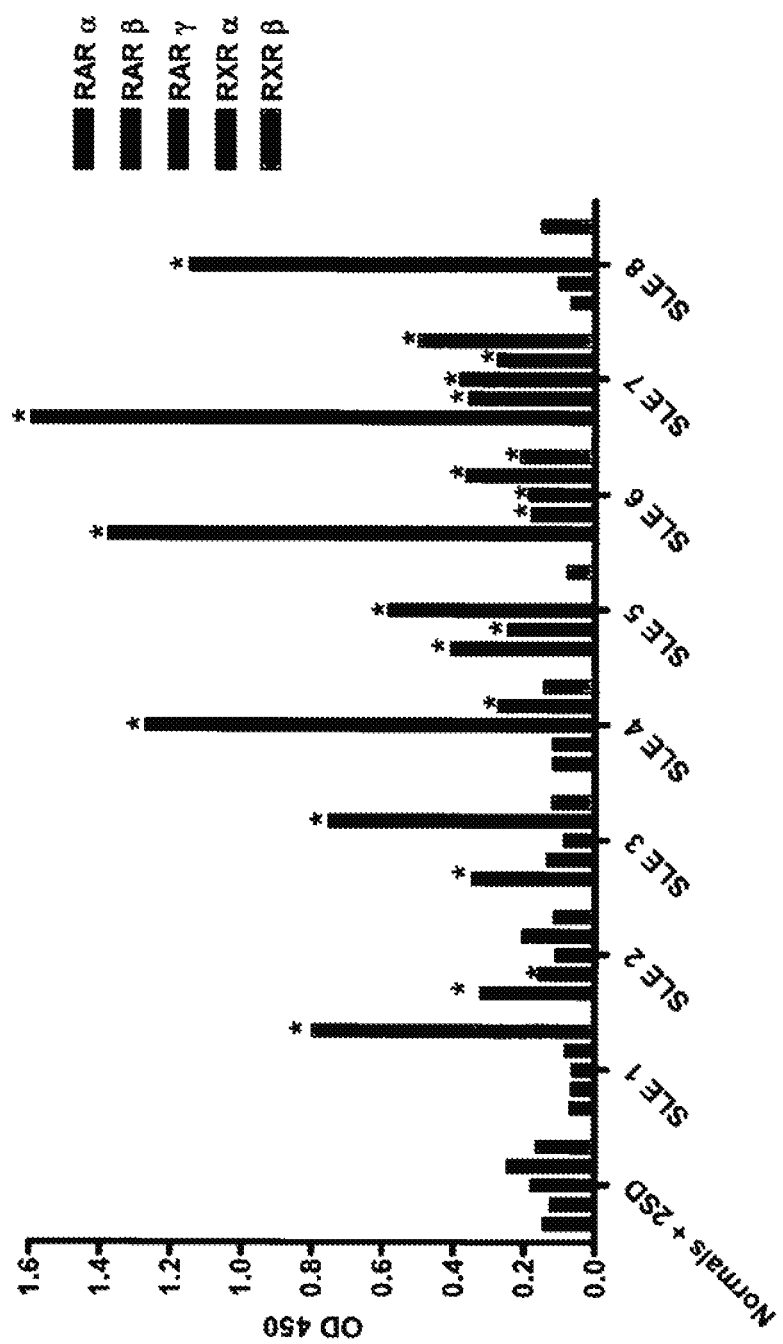

US 9,181,345 B2

METHODS OF TREATING LUPUS

This application is a continuation of U.S. application Ser. No. 12/598,524, filed Jun. 1, 2010, said application Ser. No. 12/598,524 is a U.S. National Stage application of International Application No. PCT/US2008/62639, filed May 5, 2008, and is a continuation of International Application No. PCT/US2007/24941, filed Dec. 6, 2007; and a continuation of International Application No. PCT/US2007/24947, filed Dec. 6, 2007; and claims the benefit under 35 U.S.C. §119(e) of U.S. Provisional Application Ser. No. 60/924,219, filed May 3, 2007; U.S. Provisional Application Ser. No. 60/924,220, filed May 3, 2007; U.S. Provisional Application Ser. No. 60/924,584, filed May 21, 2007; U.S. Provisional Application Ser. No. 60/960,187, filed Sep. 19, 2007; U.S. Provisional Application Ser. No. 60/996,176, filed Nov. 5, 2007; U.S. Provisional Application Ser. No. 60/996,174, Nov. 5, 2007; U.S. Provisional Application Ser. No. 60/996,219, filed Nov. 6, 2007; U.S. Provisional Application Ser. No. 60/996,820, filed Dec. 6, 2007; and U.S. Provisional Application Ser. No. 61/006,963, filed Feb. 8, 2008, each of which is incorporated by reference in its entirety.

FIELD OF THE INVENTION

The present invention relates to auto-antibodies associated with autoimmune disease and methods employing such auto-antibodies.

BACKGROUND OF THE INVENTION

The present invention encompasses auto-antibodies present in patients having an autoimmune disease. The auto-antibodies can be used in, for example, methods of treating patients, methods of diagnosing patients, methods of monitoring disease progression of patients, and methods of prognosing patients.

SUMMARY OF THE INVENTION

An embodiment of the invention encompasses a method of treating a patient having a type I IFN or IFNα-related autoimmune disorder. An agent that binds to and modulates type I IFN or IFNα activity is administered to the patient. The patient having the autoimmune disorder comprises auto-antibodies that bind at least any two auto-antigens which may be: (a) Myxovirus (influenza virus) resistance 1, interferon-inducible protein p78; (b) surfeit 5, transcript variant c; (c) proteasome (prosome, macropain) activator subunit 3 (PA28 gamma; Ki) transc; (d) retinoic acid receptor, alpha; (e) Heat shock 10 kDa protein 1 (chaperonin 10); (f) tropomyosin 3; (g) pleckstrin homology-like domain, family A, member 1; (h) cytoskeleton-associated protein 1; (i) Sjogren syndrome antigen A2 (60 kDa, ribonucleoprotein auto-antigen SS-A/Ro); (j) NADH dehydrogenase (ubiquinone) 1, alpha/beta subcomplex 1, 8 kDa; (k) NudE nuclear distribution gene E homolog 1 (A. nidulans); MutL homolog 1, colon cancer, nonpolyposis type 2 (E. coli); (m) leucine rich repeat (in FLII) interacting protein 2; (n) tropomyosin 1 (alpha); (o) spastic paraplegia 20, spartin (Troyer syndrome); (p) preimplantation protein, transcript variant 1; (r) mitochondrial ribosomal protein L45; and (s) fumarate hydratase. The agent reduces number or levels of the auto-antibodies that bind the at least any two auto-antigens in the patient.

Another embodiment of the invention encompasses a method of diagnosing a patient as having a type I IFN or IFN α-related autoimmune disorder. The presence or absence of auto-antibodies is detected in a sample of the patient. The auto-antibodies may bind to any two of (a) Myxovirus (influenza virus) resistance 1, interferon-inducible protein p78; (b) surfeit 5, transcript variant c; (c) proteasome (prosome, macropain) activator subunit 3 (PA28 gamma; Ki) transc; (d) retinoic acid receptor, alpha; (e) Heat shock 10 kDa protein 1 (chaperonin 10); (f) tropomyosin 3; (g) pleckstrin homology-like domain, family A, member 1; (h) cytoskeleton-associated protein 1; (i) Sjogren syndrome antigen A2 (60 kDa, ribonucleoprotein auto-antigen SS-A/Ro); (j) NADH dehydrogenase (ubiquinone) 1, alpha/beta subcomplex 1, 8 kDa; (k) NudE nuclear distribution gene E homolog 1 (A. nidulans); (l) MutL homolog 1, colon cancer, nonpolyposis type 2 (E. coli); (m) leucine rich repeat (in FLII) interacting protein 2; (n) tropomyosin 1 (alpha); (o) spastic paraplegia 20, spartin (Troyer syndrome); (p) preimplantation protein, transcript variant 1; (r) mitochondrial ribosomal protein L45; and (s) fumarate hydratase. Detecting the presence of the auto-antibodies diagnoses the patient as having the autoimmune disorder.

A further embodiment of the invention encompasses a method of monitoring autoimmune disorder progression of a patient receiving treatment with a therapeutic agent that binds to and modulates type I IFN activity. Auto-antibodies are identified in a first sample of a patient. The auto-antibodies may bind at least any two auto-antigens which may be: (a) Myxovirus (influenza virus) resistance 1, interferon-inducible protein p78; (b) surfeit 5, transcript variant c; (c) proteasome (prosome, macropain) activator subunit 3 (PA28 gamma; Ki) transc; (d) retinoic acid receptor, alpha; (e) Heat shock 10 kDa protein 1 (chaperonin 10); (f) tropomyosin 3; (g) pleckstrin homology-like domain, family A, member 1; (h) cytoskeleton-associated protein 1; (i) Sjogren syndrome antigen A2 (60 kDa, ribonucleoprotein auto-antigen SS-A/Ro); (j) NADH dehydrogenase (ubiquinone) 1, alpha/beta subcomplex 1, 8 kDa; (k) NudE nuclear distribution gene E homolog 1 (A. nidulans); (l) MutL homolog 1, colon cancer, nonpolyposis type 2 (E. coli); (m) leucine rich repeat (in FLIT) interacting protein 2; (n) tropomyosin 1 (alpha); (o) spastic paraplegia 20, spartin (Troyer syndrome); (p) preimplantation protein, transcript variant 1; (r) mitochondrial ribosomal protein L45; and (s) fumarate hydratase. A therapeutic agent that binds to and modulates type I IFN activity is administered. Auto-antibodies are identified in a second sample from the patient. The auto-antibodies in the first and second sample from the patient are compared. A variance in the auto-antibodies in the first and second sample indicates a level of efficacy of the therapeutic agent that binds to and modulates type I IFN activity.

Yet a further embodiment of the invention encompasses a method of prognosing a patient having a type I IFN or IFNα-mediated autoimmune disorder. Presence or absence of auto-antibodies is identified in a patient. The auto-antibodies may bind auto-antigens including: (a) Myxovirus (influenza virus) resistance 1, interferon-inducible protein p78; (b) surfeit 5, transcript variant c; (c) proteasome (prosome, macropain) activator subunit 3 (PA28 gamma; Ki) transc; (d) retinoic acid receptor, alpha; (e) Heat shock 10 kDa protein 1 (chaperonin 10); (f) tropomyosin 3; (g) pleckstrin homology-like domain, family A, member 1; (h) cytoskeleton-associated protein 1; (i) Sjogren syndrome antigen A2 (60 kDa, ribonucleoprotein auto-antigen SS-A/Ro); (j) NADH dehydrogenase (ubiquinone) 1, alpha/beta subcomplex 1, 8 kDa; (k) NudE nuclear distribution gene E homolog 1 (A. nidulans); (l) MutL homolog 1, colon cancer, nonpolyposis type 2 (E. coli); (m) leucine rich repeat (in FLJI) interacting protein 2; (n) tropomyosin 1 (alpha); (o) spastic paraplegia 20, spartin (Troyer syndrome); (p) preimplantation protein, transcript variant 1; (r) mitochondrial ribosomal protein L45; (s) Lin-28 homolog (*C. elegans*); (t) heat shock 90 kDa protein 1, alpha; (u) dom-3 homolog Z (*C. elegans*); (v) dynein, cytoplasmic, light intermediate polypeptide 2; (w) Ras-related C3 botulinum toxin substrate 1 (rho family, small GTP binding protein); (x) synovial sarcoma, X breakpoint 2, transcript variant 2; (y) moesin; (z) homer homolog (Drosophila), transcript variant 1; (aa) GCN5 general control of amino-acid synthesis 5-like 2 (yeast); (bb) eukaryotic translation elongation factor 1 gamma; (cc) eukaryotic translation elongation factor 1, delta; (dd) DNA-damage-inducible transcript 3; (ee) CCAAT/enhancer binding protein (C/EBP) gamma; and (ff) fumarate hydratase. The presence and levels of the auto-antibodies in the sample prognoses the autoimmune disorder.

In yet another embodiment of the invention is a method of treating a patient having a type I IFN or IFNα-related autoimmune disorder. An agent that binds to and modulates type I IFN or IFNα activity is administered. The patient having the autoimmune disorder comprises auto-antibodies that bind to at least a retinoic acid receptor/retinoid X receptor (RA(X)R). The agent reduces number or levels of the auto-antibodies that bind the (RA(X)R).

In another embodiment of the invention is a method of diagnosing a patient as having a type I IFN or IFNα-related autoimmune disorder. Presence or absence of auto-antibodies is detected in a sample of a patient. The auto-antibodies bind at least a retinoic acid/retinoid X receptor (RA(X)R).

In a further embodiment of the invention is a method of monitoring autoimmune disorder progression of a patient receiving treatment with a therapeutic agent that binds to and modulates type I IFN or IFNα activity. Auto-antibodies in a first sample of a patient are identified. The auto-antibodies bind at least a retinoic acid/retinoid X receptor (RA(X)R). A therapeutic agent that binds to and modulates type I IFN or IFNα activity is administered. The auto-antibodies in a second sample from the patient are identified. The auto-antibodies in the first and the second sample from the patient are compared. A variance in the auto-antibodies in the first and second sample indicates a level of efficacy of the therapeutic agent that binds to and modulates type I IFN or IFNα activity.

In yet a further embodiment of the invention is a method of prognosing a patient having a type 1 IFN or IFNα-mediated autoimmune disorder. Presence or absence of auto-antibodies in a sample of a patient are identified. The auto-antibodies bind at least a retinoic acid/retinoid X receptor (RA(X)R) in the sample of the patient. The presence and levels of the autoantibodies in the sample prognoses the autoimmune disorder.

BRIEF DESCRIPTION OF THE FIGURES

FIGS. 9 and 9b: IFNα serum activity correlates with number and intensity of autoantibodies, detected by Luminex. Graphical representation of the data (a) and autoantibodies detected in the assay (b) are presented.

FIG. 12: Autoantibodies against multiple members of the RA(X)R families of proteins are present in SLE patient sera.

DETAILED DESCRIPTION

Figure 1:
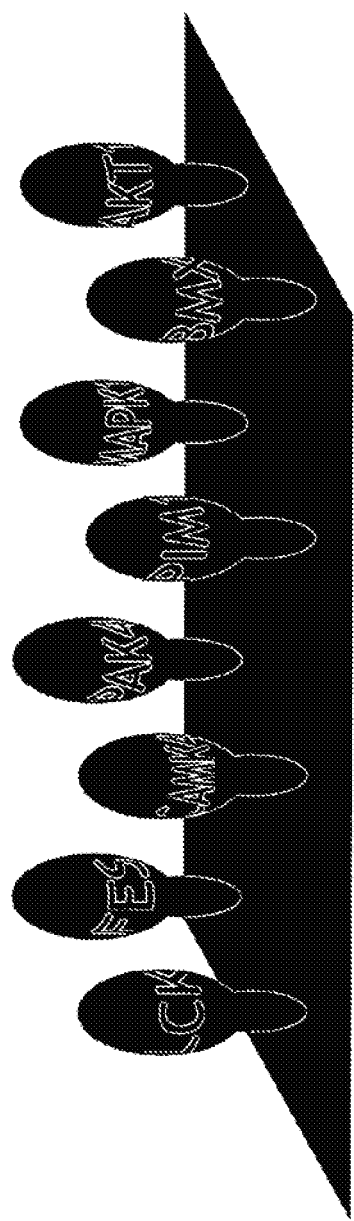
FIG. 1: Schematic representation of auto-antigen array used to identify auto-antibodies present in SLE patients.

The invention encompasses methods of treating, diagnosing, prognosing, and monitoring autoimmune disorder progression in patients. The patient may have the disease, disorder, or condition as a result of experimental research, e.g., it may be an experimental model developed for the disease, disorder, or condition. Alternatively, the patient may have the disease, disorder, or condition in the absence of experimental manipulation. Patients include humans, mice, rats, horses, pigs, cats, dogs, and any animal used for research.

A type I IFN or IFNα-mediated disorder may be any disorder in which any one or more type I IFN or IFNα subtype is dysregulated, e.g., the type I IFN or IFNα subtype is overexpressed or levels of any type I IFN or IFNα subtype are elevated in the patient. The IFNα or type-I IFN subtypes may include any one, any more than one, more than two, more than three, more than four, more than five, more than six, more than seven, more than eight, more than nine, or more than ten IFNα or type-I IFN subtypes. These IFNα or type-I IFN subtypes may include IFNα1, IFNα2, IFNα4, IFNα5, IFNα6, IFNα7, IFNα8, IFNα10, IFNα14, IFNα17, IFNα21, IFNβ, or IFNω. The IFNα or type-I IFN subtypes may include IFNα1, IFNα2, IFNα8, and IFNα14. Alternatively, the IFNα or type-I IFN subtypes may include IFNα1, IFNα2, IFNα4, IFNα5, IFNα8, IFNα10, and IFNα21. The overexpression or elevated levels of the any one or more type I IFN or IFNα subtype may be by at least 10%, 15%, 20%, 25%, 30%, 35%, 40%, 50%, 60%, 70%, 75%, 80%, 90%, 95%, 100%, 125%, 150%, 200%, or 500% relative to a healthy individual or to a healthy tissue in the patient, e.g., in non-lesional skin of a psoriasis patient.

The autoimmune disorder may be any one of systemic lupus erythematosus, insulin dependent diabetes mellitus, inflammatory bowel disease (including Crohn's disease, ulcerative colitis, and Celiac's disease), multiple sclerosis, psoriasis, autoimmune thyroiditis, rheumatoid arthritis, glomerulonephritis, idiopathic inflammatory myositis, Sjogren's syndrome, vasculitis, dermatomyositis, polymyositis, inclusion body myositis, and sarcoidosis.

The patient having the autoimmune disorder may have auto-antibodies that bind to auto-antigens. The auto-antigens to which these auto-antibodies bind may be any of the auto-antigens listed in Table 2, or Table 4, or Table 5, or Table 9. The auto-antigens may be all the auto-antigens listed in Table 2, or all the auto-antigens listed in Table 4, or all the auto-antigens listed in Table 5, or all the auto-antigens in Table 9. If the auto-antigens are a subset of the auto-antigens listed in any one of Tables 2, 4, 5, or 9 the auto-antigens may be (a) Myxovirus (influenza virus) resistance 1, interferon-inducible protein p78; (b) surfeit 5, transcript variant c; (c) proteasome (prosome, macropain) activator subunit 3 (PA28 gamma; Ki) transc; (d) retinoic acid receptor, alpha; (e) Heat shock 10 kDa protein 1 (chaperonin 10); (f) tropomyosin 3; (g) pleckstrin homology-like domain, family A, member 1; (h) cytoskeleton-associated protein 1; (i) Sjogren syndrome antigen A2 (60 kDa, ribonucleoprotein auto-antigen SS-A/Ro); (j) NADH dehydrogenase (ubiquinone) 1, alpha/beta subcomplex 1, 8 kDa; (k) NudE nuclear distribution gene E homolog 1 (*A. nidulans*); (l) MutL homolog 1, colon cancer, nonpolyposis type 2 (*E. coli*); (m) leucine rich repeat (in FLII) interacting protein 2; (n) tropomyosin 1 (alpha); (o) spastic paraplegia 20, spartin (Troyer syndrome); (p) preimplantation protein, transcript variant 1; (r) mitochondrial ribosomal protein L45; and (s) fumarate hydratase. The auto-antigens may be those highlighted in gray in Table 2. The auto-antigens may be those in bold in Table 2. The auto-antigens may be (a) Myxovirus (influenza virus) resistance 1 and interferon-inducible protein p78; and (b) surfeit 5, transcript variant c. The auto-antigens may be (a) Myxovirus (influenza virus) resistance 1, interferon-inducible protein p78; (b) surfeit 5, transcript variant c; and (c) proteasome (posome, macropain) activator subunit 3 (PA28 gamma; Ki) transc. The auto-antigens may be (a) Myxovirus (influenza virus) resistance 1, interferon-inducible protein p78; (b) surfeit 5, transcript variant c; (c) proteasome (prosome, macropain) activator subunit 3 (PA28 gamma; Ki) transc; and (d) retinoic acid receptor, alpha. The auto-antigens may be (a) Myxovirus (influenza virus) resistance 1, interferon-inducible protein p78; (b) surfeit 5, transcript variant c; (c) proteasome (prosome, macropain) activator subunit 3 (PA28 gamma; Ki) transc; (d) retinoic acid receptor, alpha; and (e) Heat shock 10 kDa protein 1 (chaperonin 10). The auto-antigens may be (a) Myxovirus (influenza virus) resistance 1, interferon-inducible protein p78; (b) surfeit 5, transcript variant c; (c) proteasome (prosome, macropain) activator subunit 3 (PA28 gamma; Ki) transc; (d) retinoic acid receptor, alpha; (e) Heat shock 10 kDa protein 1 (chaperonin 10); and (f) tropomyosin 3. The autoantigens may be any 1, 2, 3, 4, 5, 6, 7, 8, 9, 10, 11, 12, 13, 14, 15, or 16 of proteasome activator complex subunit 3 (PSME3), tropomysin 3 (TPM3), retinoic acid receptor, alpha (RARα), fumarate hydratase (FH), ribosomal protein, large, P1 (RPLP1), Sjogren syndrome antigen A2 (SSA2), heat shock 90 kDa protein 1, alpha (HSPCA), pyrroline-5-carboxylate reductase 1, transcript variant (PYCR1), cytoskeleton associated protein 1 (CKAP1), spastic paraplegia 20, spartin, Troyer syndrome (SPG20), ras-related C3 botulinum toxin substrate 1, rho family (RAC1), lactate dehydrogenase B (LDHB), oxysterol binding protein-like 9, transcript variant (OSBPL9), moesin (MSN), pleckstrin homology-like domain, family A, member 1 (PHLDA1), and mammalian homolog of Yeast MOB1 (PRE13). The autoantigens may be any 1, 2, 3, 4, 5, 6, 7, 8, 9, 10, 11, 12, 13, 14, 15, 16, or 17 of PSME3, TPM3, RARα, FH, RPLP1, SSA2, HSPCA, PYCR1, CKAP1, SPG20, RAC1, LDHB, OSBPL9, MSN, PHLDA1, PRE13, and hydroxyacyl glutathion hydrolase-like (HAGHL). The autoantigens may be any 1, 2, 3, 4, 5, 6, 7, 8, 9, 10, 11, 12, 13, 14, 15, 16, 17, 18, 19, 20, 21, 22, 23, or 24 of ankyrin repeat domain 13; ATP synthase, H+ transporting, mitochondrial F1 complex, beta polypeptide; chromosome 7 open reading frame 22; hypothetical protein DJ1042K10.2; eukaryotic translation elongation factor 1 gamma; fumarate hydratase; hepatocellular carcinoma-associated antigen 127; isopentenyl-diphosphate delta isomerase; macrophage migration inhibitory factor (glycosylation-inhibiting factor); mitochondrial ribosomal protein L45; moesin; oxysterol binding protein-like 9, transcript variant 1; protein phosphatase 1, regulatory (inhibitor) subunit 2 pseudogene 9; proteasome (prosome, macropain) activator subunit 3 (PA28 gamma; Ki), transc; ras-related C3 botulinum toxin substrate 1 (rho family, small GTP binding protein; RIO kinase 2 (yeast); ribosomal protein, large, P1; Sjogren syndrome antigen A2 (60 kDa, ribonucleoprotein autoantigen SS-A/Ro); synovial sarcoma, X breakpoint 2, transcript variant 2; serine/threonine kinase 16; TBC1 domain family, member 2; tudor and KH domain containing protein; target of myb1 (chicken); and/or urridine monophosphate kinase. The autoantigens may be any 1, 2, 3, 4, 5, 6, 7, 8, 9, 10, 11, 12, or 13 of ankyrin repeat domain 13; ATP synthase, H+ transporting, mitochondrial F1 complex, beta polypeptide; fumarate hydratase; moesin; oxysterol binding protein-like 9, transcript variant 1; proteasome (prosome, macropain) activator subunit 3 (PA28 gamma; Ki), transc; ribosomal protein, large, P1; Sjogren syndrome antigen A2 (60 kDa, ribonucleoprotein autoantigen SS-A/Ro); synovial sarcoma, X breakpoint 2, transcript variant 2; serine/threonine kinase 16; TBC1 domain family, member 2; tudor and KH domain containing protein; and/or target of myb1 (chicken). The autoantigens may be any 1, 2, 3, 4, 5, 6, or 7 of fumarate hydratase; proteasome (prosome, macropain) activator subunit 3 (PA28 gamma; Ki), transc; ribosomal protein, large, P1; Sjogren syndrome antigen A2 (60 kDa, ribonucleoprotein autoantigen SS-A/Ro); pyrroline-5-carboxylate reductase 1, transcript variant 1; retinoic acid receptor, alpha; and/or tropomyosin 3. The autoantigens may be any 1, 2, 3, or 4 of fumarate hydratase; proteasome (prosome, macropain) activator subunit 3 (PA28 gamma; Ki), trans; ribosomal protein, large, P1; and Sjorgren syndrome antigen A2 (60 kDa, ribonucleoprotein autoantigen SS-A/Ro). The autoantigens may be any 1, 2, or 3 of fumarate hydratase; proteasome (prosome, macropain) activator subunit 3 (PA28 gamma; Ki), trans; and ribosomal protein, large, P1. The autoantigens may be a member of the RA(X)R families and fumarate hydratase. The autoantigens may be any 1, 2, or 3 of proteasome (prosome, macropain) activator subunit 3 (PA28 gamma; Ki), transc; pyrroline-5-carboxylate reductase 1, transcript variant 1; and retinoic acid receptor, alpha. The autoantigens may be any 1, 2, 3, 4, 5, 6, 7, or 8 of fumarate hydratase; proteasome (prosome, macropain) activator subunit 3 (PA28 gamma; Ki), transc; ribosomal protein, large, P1; Sjogren syndrome antigen A2 (60 kDa, ribonucleoprotein autoantigen SS-A/Ro); lactate dehydrogenase B; pyrroline-5-carboxylate reductase 1, transcript variant 1; retinoic acid receptor, alpha; and tropomyosin. The autoantigens may be any 1, 2, 3, 4, 5, or 6 of proteasome (prosome, macropain) activator subunit 3 (PA28 gamma; Ki), transc; Sjogren syndrome antigen A2 (60 kDa, ribonucleoprotein autoantigen SS-A/Ro); cytoskeleton-associated protein 1; pyrroline-5-carboxylate reductase 1, transcript variant 1; retinoic acid receptor, alpha; and tropomyosin. The autoantigens may any subset of at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, or at least 30 of those shown in Table 9. The autoantigen may be one or more of the RA(X)R family members. The RA(X)R family members may be RARα, RARβ, RARγ, RXRα, RXRβ, RXRγ, or any isoform thereof. The RA(X)R family members may be RARα. The autoantigens may include an RA(X)R family member and any other 1, 2, 3, 4, 5, 6, 7, 8, 9, 10, 11, 12, 13, 14, 15, 16, 17, 18, 19, 20, 25, 30, or 35 autoantigens discussed above. The auto-antigens may be any at least 2, at least 3, at least 4, at least 5, at least 6, at least 7, at least 8, at least 9 at least 10, at least 11, at least 12, at least 13, at least 14, at least 15, at least 20, at least 25, at least 30, at least 35, at least 40, or at least 45 of those listed in Tables 2, 4, and/or 5, and/or 9.

The patients may also exhibit any of a number of symptoms as discussed in, e.g., provisional patent application Methods of Treating Systemic Lupus Erythematosis filed Apr. 16, 2007.

The patients may further comprise a type I IFN or IFNα-inducible P11 marker expression profile. The type I IFN or IFNα-inducible PD marker expression profile may comprise upregulation of any group of genes induced by a type I IFN or IFNα. One or more upregulated PD markers may include any of RSAD2, HERC5, IRF7, MARCKS, LY6E, RAB8B, LILRA5, IFIT3, OAS1, IFIT1, EIF2AK2, G1P3, MX1, OAS3, STAT2, MX2, IRF2, FCHO2, IFI44, IFI44L, IL6ST, or G1P2. One or more upregulated PD markers may include any of RSAD2, HERC5, IRF7, MARCKS, LY6E, RAB8B, LILRA5, IFIT3, OAS1, IFIT1, EIF2AK2, G1P3, MX1, OAS3, STAT2, MX2, IRF2, FCHO2, IFI44, IFI44L, IL6ST, or G1P2. One or more upregulated PD markers may include any of RSAD2, HERC5, Ly6E, IFIT3, OAS1, G1P3, MX1, OAS3, or IFI44. One or more upregulated PD markers may include any of RTP4, RSAD2, HERC5, SIGLEC1, USP18, LY6E, ETV7, SERPING1, IFIT3, OAS1, HSXIAPAF1, G1P3, MX1, OAS3, IFI27, DNAPTP6, LAMP3, EPSTI1, IFI44, OAS2, IFIT2, or ISG15. One or more upregulated PD markers may include any of RTP4, RSAD2, HERC5, SIGLEC1, USP18, LY6E, ETV7, SERPING1, IFIT3, OAS1, HSXIAPAF1, G1P3, MX1, OAS3, IFI27, DNAPTP6, LAMP3, EPSTI1, IFI44, OAS2, IFIT2, or ISG15. One or more upregulated PD markers may include any of HSXIA-PAF1 or G1P3. One or more upregulated PD markers may include any of XAF1, IFI27, IFIT2, USP18, OAS1, OAS2, EPSTI1, LY6E, RSAD2, LAMP3, ISG15, SERPING1, ETV7, RTP4, IFI6, OAS3, SIGLEC1, IFIT3, DNAPTP6, MX1, HERC5, or IFI44. The type I IFN or IFNα-inducible PD marker expression profile may include any at least 2, any at least 3, any at least 4, any at least 5, any at least 6, any at least 7, any at least 8, any at least 9, any at least 10, any at least 11, any at least 12, any at least 13, any at least 14, any at least 15, any at least 16, any at least 17, any at least 18, any at least 19, any at least 20, any at least 21, any at least 22, any at least 23, any at least 24, any at least 25, any at least 26, any at least 27, any at least 28, any at least 29, any at least 30, any at least 40, or any at least 50 of the genes induced by type I IFN or IFNα. The type I IFN or IFNα-inducible genes may include MX1, LY6E, IFI27, OAS1, IFIT1, IFI6, IFI44L, ISG15, LAMP3, OASL, RASD2, and IFI44. The type I IFN or IFNα-inducible genes may include IFI44, IFI27, IFI44L, DNAPTP6, LAMP3, LY6E, RSAD2, HERC5, IFI6, ISG15, OAS3, SIGLEC1, OAS2, USP18, RTP4, IFIT1, MX1, OAS1, EPSTI1, PLSCR1, and IFRG28. The type I IFN or IFNα-inducible genes may include any at least 2, any at least 3, any at least 4, any at least 5, any at least 6, any at least 7, any at least 8, any at least 9, any at least 10, or any at least 11, or any at least 12, or any at least 13, or any at least 14, or any at least 15, or any at least 16, or any at least 17, or any at least 18, or any at least 19, or at least 20, or any at least 21, or any at least 22, or any at least 23, or any at least 24, or any at least 25, or any at least 26, or any at least 27, or any at least 28, or any at least 29, or any at least 30 of LAMP3, DNAPTP6, FLJ31033, HERC6, SERPING1, EPST11, RTP4, OASL, FBXO6, IFIT2, IFI44, OAS3, BATF2, ISG15, IRF7, RSAD2, IFI35, OAS1, LAP3, IFIT1, IFIT5, PLSCR1, IFI44L, MS4A4A, GALM, UBE2L6, TOR1B, SAMD9L, HERC5, TDRD7, TREX1, PARP12, and AXUD1. The type I IFN or IFNα-inducible genes may include any at least 2, any at least 3, any at least 4, any at least 5, any at least 6, any at least 7, any at least 8, any at least 9, any at least 10, or any at least 11, or any at least 12, or any at least 13, or any at least 14, or any at least 15, or any at least 16, or any at least 17, or any at least 18, or any at least 19, or any at least 20, or any at least 21, or any at least 22, or any at least 23, or any at least 24, or any least 25, or any at least 26, or any at least 27, or any at least 28, or any at least 29, or any at least 30, or any at least 40, or any at least 50, or any at least 60, or any at least 70, or any at least 80, or any at least 90, or any at least 100 of the type I IFN or IFNα-inducible genes identified in U.S. provisional patent application Ser. No. 60/873,008 filed Dec. 6, 2006 or provisional patent application 60/907,762 filed Apr. 16, 2007 or provisional patent application Ser. No. 60/924,219 filed 3 May 2007, or provisional patent application Ser. No. 60/924,584 filed 21 May 2007, or provisional patent application Ser. No. 60/960,187 filed 19 Sep. 2007, or provisional patent application entitled "interferon alpha-induced pharmacodynamic markers" filed Nov. 6, 2007.

Up-regulation of genes induced by a type I IFN or IFNα includes any increased level of type I IFN or IFNα genes expression or activity that is at least 10%, at least 15%, at least 20%, at least 25%, at least 30%, at least 40%, at least 50%, at least 60%, at least 75%, at least 80%, at least 85%, at least 90%, at least 95%, at least 96%, at least 97%, at least 98%, at least 99%, or at least 100% relative to a control sample (obtained from the patient or a healthy individual).

The patient may further comprise downregulated type I IFN or IFNα PD marker(s). The downregulated PD markers may include any one, any two, any three, any four, any five, any six, or any seven of CYP1B1, TGST1, RRAGD, IRS2, MGST1, TGFBR3, and RGS2.

The patient may further comprise upregulation of expression of IFNα receptors, either IFNAR1 or IFNAR2, or both, or TNFα, or IFNγ, or IFNγ receptors (either IFNGR1, IFNGR2, or both IFNGR1 and IFNGR2). The patient may simply be identified as one who comprises upregulation of expression of IFNα receptors, either IFNAR1 or IFNAR2, or both, or TNFα, or IFNγ, or IFNγ receptors (either IFNGR1, IFNGR2, or both IFNGR1 and IFNGR2).

The upregulation of the type I IFN or IFNα-inducible PD markers, or upregulation of expression of IFNα or type-I IFN subtypes, or upregulation of IFNα receptors in the patient may be by any degree relative to that of a sample from a control (which may be from a sample that is not disease tissue of the patient or from a healthy person not afflicted with the disease or disorder). The degree upregulation may be at least 10%, at least 15%, at least 20%, at least 25%, at least 30%, at least 40%, at least 50%, at least 60%, at least 70%, at least 75%, at least 80%, at least 90%, at least 100%, at least 125%, at least 150%, or at least 200%, or at least 300%, or at least 400%, or at least 500% that of the control or control sample.

If the therapeutic agent is a biological agent, it may be an antibody specific for any subtype(s) of type I IFN or IFNα. For instance, the antibody may be specific for any one of IFNα1, IFNα2, IFNα4, IFNα5, IFNα6, IFNα7, IFNα8, IFNα10, IFNα14, IFNα17, IFNα21, IFNβ, or IFNω. Alternatively, the antibody may be specific for any two, any three, any four, any five, any six, any seven, any eight, any nine, any ten, any eleven, any twelve type I IFN of IFNα subtypes. If the antibody is specific for more than one type I IFN subtype, the antibody may be specific for IFNα1, IFNα2, IFNα4, IFNα5, IFNα8, IFNα10, and IFNα21; or it may be specific for IFNα1, IFNα2, IFNα4, IFNα5, IFNα8, and IFNα10; or it may be specific for IFNα1, IFNα2, IFNα4, IFNα5, IFNα8, and IFNα21; or it may be specific for IFNα1, IFNα2, IFNα4, IFNα5, IFNα10, and IFNα21. Antibodies specific for type I IFN or IFNα include MEDI-545, any biologic or antibody other than MEDI-545, antibodies described in U.S. patent application Ser. No. 11/009,410 filed Dec. 10, 2004 and Ser. No. 11/157,494 filed Jun. 20, 2005, 9F3 and other antibodies described in U.S. Pat. No. 7,087,726, NK-2 and YOK5/19 (WO 84/03105), LO-22 (U.S. Pat. No. 4,902,618), 144 BS (U.S. Pat. No. 4,885,166), and EBI-1, EBI-2, and EBI-3 (EP 119476). A therapeutic agent that modulates IFNα activity may neutralize IFNα activity.

A second agent other than the agent that binds to modulates IFNα activity may be administered to the patient. Second agents include, but are not limited to non-steroidal anti-inflammatory drugs such as ibuprofen, naproxen, sulindac, diclofenac, piroxicam, ketoprofen, diflunisal, nabumetone, etodolac, and oxaprozin, indomethacin; anti-malarial drugs such as hydroxychloroquine; corticosteroid hormones, such as prednisone, hydrocortisone, methylprednisolone, and dexamethasone; methotrexate; immunosuppressive agents, such as azathioprine and cyclophosphamide; and biologic agents that, e.g., target T cells such as Alefacept and Efalizumab, or target TNFα, such as, Enbrel, Remicade, and Humira.

Administration of the agent that binds to and modulates type I IFN or IFNα to the patient reduces levels of the auto-antibodies in the patient. Levels of the auto-antibodies may be reduced to levels at least 90% those before administration of the therapeutic agent. Levels of the auto-antibodies may be reduced to levels at least 80%, at least 75%, at least 70%, at least 65%, at least 60%, at least 50%, at least 40%, at least 30%, at least 25%, at least 20%, at least 15%, at least 10%, at least 5%, or at least 1% those before administration of the therapeutic agent. The reduction in levels may refer to a cumulative reduction in overall level of all autoantibodies in the patient. The reduction in levels may refer to a reduction in levels of any at least 1, any at least 2, any at least 3, any at least 4, any at least 5, any at least 6, any at least 7, any at least 8, any at least 9 any at least 10, any at least 11, any at least 12, any at least 15, any at least 20, or at least any 25 autoantibodies in the patient. The reduction in levels may refer to a reduction of the overall level of autoantibodies in the patient to within about 90% to within about 80%, to within about 75%, to within about 70%, to within about 65%, to within about 60%, to within about 55%, to within about 50%, to within about 45%, to within about 40%, to within about 35%, to within about 30%, to within about 25%, to within about 20%, to within about 15%, to within about 10%, to within about 9%, to within about 8%, to within about 7%, to within about 6%, to within about 5%, to within about 4%, to within about 3%, to within about 2%, or to within about 1% of those of normal healthy controls.

If the agent that binds to and modulates type I IFN or IFNα activity is a biologic agent, such as an antibody, the agent may reduce the levels of auto-antibodies in the patient at doses of 0.3 to 30 mg/kg, 0.3 to 10 mg/kg, 0.3 to 3 mg/kg, 0.3 to 1 mg/kg, 1 to 30 mg/kg, 3 to 30 mg/kg, 5 to 30 mg/kg, 10 to 30 mg/kg, 1 to 10 mg/kg, 3 to 10 mg/kg, or 1 to 5 mg/kg.

The agent may not only reduce levels of auto-antibodies in the patient, but may further neutralize a type I IFN or IFNα-inducible PD marker expression profile. Neutralization of the type I IFN or IFNα-inducible PD marker expression profile may be a reduction in at least one, at least two, at least three, at least five, at least seven, at least eight, at least ten, at least twelve, at least fifteen, at least twenty, at least twenty five, at least thirty, at least thirty five, at least forty, at least forty five, or at least fifty genes induced by type I IFN or IFNα. Neutralization of the type I IFN or IFNα-inducible profile is a reduction of at least 2%, at least 3%, at least 4%, at least 5%, at least 7%, at least 8%, at least 10%, at least 15%, at least 25%, at least 30%, at least 35%, at least 40%, at least 45%, at least 50%, at least 60%, at least 70%, at least 75%, at least 80%, or at least 90% of any of the genes induced by type I IFN or IFNα. Alternatively, neutralization of the type I IFN or IFNα-inducible profile refers to a reduction of expression of type I IFN or IFNα-inducible genes that is within at most 50%, at most 45%, at most 40%, at most 35%, at most 30%, at most 25%, at most 20%, at most 15%, at most 10%, at most 5%, at most 4%, at most 3%, at most 2%, or at most 1% of expression levels of those type I IFN or IFNα-inducible genes in a control sample. The agent that binds to and modulates type I IFN or IFNα activity may further or alternatively neutralize expression of one or more type I IFN or IFNα subtypes. The IFNα or type-I IFN subtypes may include any more than one, more than two, more than three, more than four, more than five, more than six, more than seven, more than eight, more than nine, or more than ten IFNα or type-I IFN subtypes. These subtypes may include IFNα1, IFNα2, IFNα4, IFNα5, IFNα$_6$, IFNα7, IFNα8, IFNα10, IFNα14, IFNα17, IFNα21, IFNβ, or IFNω. These subtypes may include all of IFNα1, IFNα2, IFNα8, and IFNα14. Neutralization of the IFNα or type-I IFN subtypes may be a reduction of at least 2%, at least 3%, at least 4%, at least 5%, at least 7%, at least 8%, at least 10%, at least 15%, at least 25%, at least 30%, at least 35%, at least 40%, at least 45%, at least 50%, at least 60%, at least 70%, at least 75%, at least 80%, or at least 90% of any of the at least one, at least two, at least three, at least five, at least seven, at least eight, or at least ten of the subtypes. Neutralization of the IFNα or type-I IFN subtypes may be a reduction in expression of IFNα or type-I IFN subtype genes that is within at most 50%, at most 45%, at most 40%, at most 35%, at most 30%, at most 25%, at most 20%, at most 15%, at most 10%, at most 5%, at most 4%, at most 3%, at most 2%, or at most 1% of expression levels of those IFNα or type I IFN subtypes in a control sample.

The reduction of the levels of the auto-antibodies in the patient receiving the agent may be detected by any means known in the art. For example, the auto-antibodies may be detected using protein arrays spotted with auto-antigens for which the auto-antibodies are specific. Protein arrays have been described in the art and are routinely prepared. For example, protein arrays are produced by Ciphergen Biosystems (Fremont, Calif.), Packard BioScience Company (Meriden Conn.), Zyomyx (Hayvard, Calif.), Phylos (Lexington, Mass.) and Procognia (Sense Proteomic Limited) (Maidenhead, Berkshire, UK). Examples of such protein arrays are described in International publication WO200157198 (Blackburn et al., "Methods of Generating Protein Expression Arrays and Use Thereof in Rapid Screening," Jan. 31, 2001); U.S. Pat. No. 6,225,047 (Hutchens and Yip, "Use of retentate chromatography to generate difference maps," May 1, 2001); International publication WO 99/51773 (Kuimelis and Wagner, "Addressable protein arrays," Oct. 14, 1999); U.S. Pat. No. 6,329,209 (Wagner et al., "Arrays of protein-capture agents and methods of use thereof," Dec. 11, 2001), International publication WO 00/56934 (Englert et al., "Continuous porous matrix arrays," Sep. 28, 2000), United States patent publication US 2003/0180957 A 1 (Koopman et al., "Target and method," Sep. 25, 2003) and United States patent publication US 2003/0173513 A1 (Koopman et al., "Probe for mass spectrometry," Sep. 18, 2003). Other assays that can be used to detect reduction of levels of auto-antibodies that bind to auto-antigens include immunoprecipitation and pull-down assays.

If type I IFN or IFNα-inducible PD marker expression or activity is to be detected in the patient before or after administering the agent, expression or activity may be determined by any means known in the art. For example, up- or down-regulation of gene expression may be detected by determining mRNA levels. mRNA expression may be determined by northern blotting, slot blotting, quantitative reverse transcriptase polymerase chain reaction, or gene chip hybridization techniques. See U.S. Pat. Nos. 5,744,305 and 5,143,854 for examples of making nucleic acid arrays for gene chip hybridization techniques. Type I IFN or IFNα-inducible PD marker expression or activity may be determined by detecting protein levels. Methods for detecting protein expression levels include immuno-based assays such as enzyme-linked immunosorbant assays, western blotting, protein arrays, and silver staining. Type I IFN or IFNα-inducible PD marker expression or activity may be determined by protein activity including, but not limited to, detectable phosphorylation activity, de-phosphorylation activity, or cleavage activity. Furthermore, up- or down-regulation of gene expression or activity of IFNα-inducible PD markers may be determined by detecting any combination of these gene expression levels or activities.

Another embodiment encompasses diagnosis of a patient with an autoimmune disorder. Such a patient may exhibit one or more symptoms of an autoimmune disorder or may not exhibit any symptoms at all. Samples may be obtained from the patient for detection of auto-antibodies. Samples include any biological fluid or tissue, such as whole blood, saliva, urine, synovial fluid, bone marrow, cerebrospinal fluid, nasal secretions, sputum, amniotic fluid, bronchoalveolar lavage fluid, peripheral blood mononuclear cells, total white blood cells, lymph node cells, spleen cells, tonsil cells, or skin. The samples may be obtained by any of the well known means in the art.

Presence or absence of auto-antibodies is detected in the sample. The auto-antigens to which these auto-antibodies bind may be any of the auto-antigens listed in Table 2, or Table 4, Table 5, or Table 9. The auto-antigens may be all the auto-antigens listed in Table 2, or all the auto-antigens listed in Table 4, or all the auto-antigens listed in Table 5, or all the auto-antigens listed in Table 9. If the auto-antigens are a subset of the auto-antigens listed in any one of Tables 2, 4, 5, or 9 the auto-antigens may be (a) Myxovirus (influenza virus) resistance 1, interferon-inducible protein p78; (b) surfeit 5, transcript variant c; (c) proteasome (prosome, macropain) activator subunit 3 (PA28 gamma; Ki) transc; (d) retinoic acid receptor, alpha; (e) Heat shock 10 kDa protein 1 (chaperonin 10); (f) tropomyosin 3; (g) pleckstrin homology-like domain, family A, member 1; (h) cytoskeleton-associated protein 1; (i) Sjogren syndrome antigen A2 (60 kDa, ribonucleoprotein auto-antigen SS-A/Ro); (j) NADH dehydrogenase (ubiquinone) 1, alpha/beta subcomplex 1, 8 kDa; (k) NudE nuclear distribution gene E homolog 1 (A. nidulans); (l) MutL homolog 1, colon cancer, nonpolyposis type 2 (E. coli); (m) leucine rich repeat (in FLIT) interacting protein 2; (n) tropomyosin 1 (alpha); (o) spastic paraplegia 20, spartin (Troyer syndrome); (p) preimplantation protein, transcript variant 1; (r) mitochondrial ribosomal protein L45; and fumarate hydratase. The auto-antigens may be those highlighted in gray in Table 2. The auto-antigens may be those in bold in Table 2. The auto-antigens may be (a) Myxovirus (influenza virus) resistance 1 and interferon-inducible protein p78; and (b) surfeit 5, transcript variant c. The auto-antigens may be (a) Myxovirus (influenza virus) resistance 1, interferon-inducible protein p78; (b) surfeit 5, transcript variant c; and (c) proteasome (prosome, macropain) activator subunit 3 (PA28 gamma; Ki) transc. The auto-antigens may be (a) Myxovirus (influenza virus) resistance 1, interferon-inducible protein p78; (b) surfeit 5, transcript variant c; (c) proteasome (prosome, macropain) activator subunit 3 (PA28 gamma; Ki) transc; and (d) retinoic acid receptor, alpha. The auto-antigens may be (a) Myxovirus (influenza virus) resistance 1, interferon-inducible protein p78; (b) surfeit 5, transcript variant c; (c) proteasome (prosome, macropain) activator subunit 3 (PA28 gamma; ki) transc; (d) retinoic acid receptor, alpha; and (e) Heat shock 10 kDa protein 1 (chaperonin 10). The auto-antigens may be (a) Myxovirus (influenza virus) resistance 1, interferon-inducible protein p78; (b) surfeit 5, transcript variant c; (c) proteasome (prosome, macropain) activator subunit 3 (PA28 gamma; Ki) transc; (d) retinoic acid receptor, alpha; (e) Heat shock 10 kDa protein 1 (chaperonin 10); and (f) tropomyosin 3. The autoantigens may be any 1, 2, 3, 4, 5, 6, 7, 8, 9, 10, 11, 12, 13, 14, 15, or 16 of PSME3, TPM3, RARα, FH, RPLP1, SSA2, HSPCA, PYCR1, CKAP1, SPG20, RAC1, LDHB, OSBPL9, MSN, PHLDA1, and PRE13. The autoantigens may be any 1, 2, 3, 4, 5, 6, 7, 8, 9, 10, 11, 12, 13, 14, 15, 16, or 17 of PSME3, TPM3, RARα, FH, RPLP1, SSA2, HSPCA, PYCR1, CKAP1, SPG20, RAC1, LDHB, OSBPL9, MSN, PHLDA1, PRE13, and HAGHL. The autoantigens may be any 1, 2, 3, 4, 5, 6, 7, 8, 9, 10, 11, 12, 13, 14, 15, 16, 17, 18, 19, 20, 21, 22, 23, or 24 of ankyrin repeat domain 13; ATP synthase, H+ transporting, mitochondrial F1 complex, beta polypeptide; chromosome 7 open reading frame 22; hypothetical protein DJ1042K10.2; eukaryotic translation elongation factor 1 gamma; fumarate hydratase; hepatocellular carcinoma-associated antigen 127; isopentenyl-diphosphate delta isomerase; macrophage migration inhibitory factor (glycosylation-inhibiting factor); mitochondrial ribosomal protein L45; moesin; oxysterol binding protein-like 9, transcript variant 1; protein phosphatase 1, regulatory (inhibitor) subunit 2 pseudogene 9; proteasome (prosome, macropain) activator subunit 3 (PA28 gamma; Ki), transc; ras-related C3 botulinum toxin substrate 1 (rho family, small GTP binding protein; RIO kinase 2 (yeast); ribosomal protein, large, P1; Sjogren syndrome antigen A2 (60 kDa, ribonucleoprotein autoantigen SS-A/Ro); synovial sarcoma, X breakpoint 2, transcript variant 2; serine/threonine kinase 16; TBC1 domain family, member 2; tudor and KH domain containing protein; target of myb1 (chicken); and/or urridine monophosphate kinase. The autoantigens may be any 1, 2, 3, 4, 5, 6, 7, 8, 9, 10, 11, 12, or 13 of ankyrin repeat domain 13; ATP synthase, H+ transporting, mitochondrial F1 complex, beta polypeptide; fumarate hydratase; moesin; oxysterol binding protein-like 9, transcript variant 1; proteasome (prosome, macropain) activator subunit 3 (PA28 gamma; Ki), transc; ribosomal protein, large, P1; Sjogren syndrome antigen A2 (60 kDa, ribonucleoprotein autoantigen SS-A/Ro); synovial sarcoma, X breakpoint 2, transcript variant 2; serine/threonine kinase 16; TBC1 domain family, member 2; tudor and KH domain containing protein; and/or target of myb1 (chicken). The autoantigens may be any 1, 2, 3, 4, 5, 6, or 7 of fumarate hydratase; proteasome (prosome, macropain) activator subunit 3 (PA28 gamma; Ki), transc; ribosomal protein, large, P1; Sjogren syndrome antigen A2 (60 kDa, ribonucleoprotein autoantigen SS-A/Ro); pyrroline-5-carboxylate reductase 1, transcript variant 1; retinoic acid receptor, alpha; and/or tropomyosin 3. The autoantigens may be any 1, 2, 3, or 4 of fumarate hydratase; proteasome (prosome, macropain) activator subunit 3 (PA28 gamma; Ki), trans; ribosomal protein, large, P1; and Sjorgren syndrome antigen A2 (60 kDa, ribonucleoprotein autoantigen SS-A/Ro). The autoantigens may be any 1, 2, or 3 of fumarate hydratase; proteasome (prosome, macropain) activator subunit 3 (PA28 gamma; Ki), trans; and ribosomal protein, large, P1. The autoantigens may be a member of the RA(X)R families and furnarate hydratase. The autoantigens may be any 1, 2, or 3 of proteasome (prosome, macropain) activator subunit 3 (PA28 gamma; Ki), transe; pyrroline-5-carboxylate reductase 1, transcript variant 1; and retinoic acid receptor, alpha. The autoantigens may be any 1, 2, 3, 4, 5, 6, 7, or 8 of fumarate hydratase; proteasome (prosome, macropain) activator subunit 3 (PA28 gamma; Ki), transc; ribosomal protein, large, P1; Sjogren syndrome antigen A2 (60 kDa, ribonucleoprotein autoantigen SS-A/Ro); lactate dehydrogenase B; pyrroline-5-carboxylate reductase 1, transcript variant 1; retinoic acid receptor, alpha; and tropomyosin. The autoantigens may be any 1, 2, 3, 4, 5, or 6 of proteasome (prosome, macropain) activator subunit 3 (PA28 gamma; Ki), transc; Sjogren syndrome antigen A2 (60 kDa, ribonucleoprotein autoantigen SS-A/Ro); cytoskeleton-associated protein 1; pyrroline-5-carboxylate reductase 1, transcript variant 1; retinoic acid receptor, alpha; and tropomyosin. The autoantigens may any subset of at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25; or at least 30 shown in Table 9. The autoantigen may be one or more RA(X)R family member. The RA(X)R family member may be RARα, RARβ, RARγ, RXRα, RXRβ, RXRγ, or any isoform thereof. The RA(X)R family member may be RARα. The autoantigens may include an RA(X)R family member and any other 1, 2, 3, 4, 5, 6, 7, 8, 9, 10, 11, 12, 13, 14, 15, 16, 17, 18, 19, 20, 25, 30, or 35 autoantigens discussed above. The auto-antigens may be any at least 2, at least 3, at least 4, at least 5, at least 6, at least 7, at least 8, at least 9 at least 10, at least 11, at least 12, at least 13, at least 14, at least 15, at least 20, at least 25, at least 30, at least 35, at least 40, or at least 45 of those listed in Tables 2, 4, and/or 5 and/or 9. The antibodies to the autoantigens may be detected with upregulation of one or more PD marker. The PD marker may include any one or more of RSAD2, HERC5, IRF7, MARCKS, LY6E, RAB8B, LILRA5, IFIT3, OAS1, IFIT1, EIF2AK2, G1P3, MX1, OAS3, STAT2, MX2, IRF2, FCHO2, IFI44, IFI44L, IL6ST, or G1P2. The PD marker may include any one or more of RSAD2, HERC5, IRF7, MARCKS, LY6E, RAB8B, LILRA5, IFIT3, OAS1, IFIT1, EIF2AK2, G1P3, MX1, OAS3, STAT2, MX2, IRF2, FCHO2, IFI44, IFI44L, 1L6ST, or G1P2. The PD marker may include any one or more of RSAD2, HERC5, Ly6E, IFIT3, OAS1, G1P3, MX1, OAS3, or IFI44. The PD marker may include any one or more of RTP4, RSAD2, HERC5, SIGLEC1, USP18, LY6E, ETV7, SERPING1, IFIT3, OAS1, HSXIAPAF1, G1P3, MX1, OAS3, IFI27, DNAPTP6, LAMP3, EPSTI1, IFI44, OAS2, IFIT2, or ISG15. The PD marker may include any one or more of RTP4, RSAD2, HERC5, SIGLEC1, USP18, LY6E, ETV7, SERPING1, IFIT3, OAS1, HSXIAPAF1, G1P3, MX1, OAS3, IFI27, DNAPTP6, LAMP3, EPSTI1, IFI44, OAS2, IFIT2, or ISG15. The PD marker may include any one or more of HSXIAPAF1 or G1P3. The PD marker may include any one or more of XAF1, IFI27, IFIT2, USP18, OAS1, OAS2, EPSTI1, LY6E, RSAD2, LAMP3, ISG15, SERPING1, ETV7, RTP4, IFI6, OAS3, SIGLEC1, IFIT3, DNAPTP6, MX1, HERC5, or IFI44.

Presence of the auto-antibodies may be detected by any means known in the art and as described above, e.g., protein arrays, immunoprecipitation, and pulldown assays. The autoimmune disorder may be any one of systemic lupus erythematosus, insulin dependent diabetes mellitus, inflammatory bowel disease (including Crohn's disease, ulcerative colitis, and Celiac's disease), multiple sclerosis, psoriasis, autoimmune thyroiditis, rheumatoid arthritis, glomerulonephritis, idiopathic inflammatory myositis, Sjogren's syndrome, vasculitis, dermatomyositis, polymyositis, inclusion body myositis, and sarcoidosis.

If a patient has been diagnosed with the autoimmune disorder and progression of the disorder is being monitored, samples from the patient may be obtained before and after administration of an agent that binds to and modulates type I IFN or IFNα activity. Auto-antibodies are identified in the (before and after agent administration) samples. The auto-antibodies in the samples are compared. Comparison may be of the number of auto-antibodies present in the samples or may be of the quantity of auto-antibodies present in the samples, or any combination thereof. Efficacy of the therapeutic agent is indicated if the number of auto-antibodies decreases in the sample obtained after administration of the therapeutic agent relative to the sample obtained before administration of the therapeutic agent. The number of auto-antibodies may decrease by at least 1, at least 2, at least 3, at least 4, at least 5, at least 6, at least 7, at least 8, at least 9, or at least 10. The level of any given auto-antibody may decrease by at least 10%, at least 20%, at least 25%, at least 30%, at least 35%, at least 40%, at least 50%, at least 60%, at least 70%, at least 80%, at least 90%, or at least 95%. The number of auto-antibodies with decreased levels may be at least 1, at least 2, at least 3, at least 4, at least 5, at least 6, at least 7, at least 8, at least 9, at least 10, at least 15, at least 20, at least 25, at least 30, or at least 35. Any combination of decreased number and decreased level of auto-antibody may indicate efficacy.

The sample obtained from the patient may be obtained prior to a first administration of the agent, i.e., the patient is naïve to the agent. Alternatively, the sample obtained from the patient may occur after administration of the agent in the course of treatment. For example, the agent may have been administered prior to the initiation of the monitoring protocol. Following administration of the agent an additional samples may be obtained from the patient and auto-antibodies in the samples are compared.

The samples may be obtained at any time before and after the administration of the therapeutic agent. The sample obtained after administration of the therapeutic agent may be obtained at least 2, at least 3, at least 4, at least 5, at least 6, at least 7, at least 8, at least 9, at least 10, at least 12, or at least 14 days after administration of the therapeutic agent. The sample obtained after administration of the therapeutic agent may be obtained at least 2, at least 3, at least 4, at least 5, at least 6, at least 7, or at least 8 weeks after administration of the therapeutic agent. The sample obtained after administration of the therapeutic agent may be obtained at least 2, at least 3, at least 4, at least 5, or at least 6 months following administration of the therapeutic agent.

Additional samples may be obtained from the patient following administration of the therapeutic agent. At least 2, at least 3, at least 4, at least 5, at least 6, at least 7, at least 8, at least 9, at least 10, at least 12, at least 15, at least 20, at least 25 samples may be obtained from the patient to monitor progression or regression of the autoimmune disorder over time. Disease progression may be monitored over a time period of at least 1 week, at least 2 weeks, at least 3 weeks, at least 4 weeks, at least 5 weeks, at least 6 weeks, at least 7 weeks, at least 2 months, at least 3 months, at least 4 months, at least 5 months, at least 6 months, at least 1 year, at least 2 years, at least 3 years, at least 4 years, at least 5 years, at least 10 years, or over the lifetime of the patient. Additional samples may be obtained from the patient at regular intervals such as at monthly, bi-monthly, once a quarter year, twice a year, or yearly intervals. The samples may be obtained from the patient following administration of the agent at regular intervals. For instance, the samples may be obtained from the patient at one week following each administration of the agent, or at two weeks following each administration of the agent, or at three weeks following each administration of the agent, or at one month following each administration of the agent, or at two months following each administration of the agent. Alternatively, multiple samples may be obtained from the patient following an or each administration of the agent.

Disease progression in a patient having an autoimmune disorder may similarly be monitored, in the absence of administration of an agent. Samples may periodically be obtained from the patient having the autoimmune disorder. Disease progression may be identified if the number of auto-antibodies increases in a later-obtained sample relative to an earlier obtained sample. The number of auto-antibodies may increase by at least 1, at least 2, at least 3, at least 4, at least 5, at least 6, at least 7, at least 8, at least 9, or at least 10. Disease progression may be identified if level of any given auto-antibody increases by at least 10%, at least 20%, at least 25%, at least 30%, at least 35%, at least 40%, at least 50%, at least 60%, at least 70%, at least 80%, at least 90%, or at least 95%. The number of auto-antibodies with increased levels may be at least 1, at least 2, at least 3, at least 4, at least 5, at least 6, at least 7, at least 8, at least 9, at least 10, at least 15, at least 20, at least 25, at least 30, or at least 35. Any combination of increased number and increased level of auto-antibody may indicate disease progression. Disease regression may also be identified in a patient having an autoimmune disorder, not treated by an agent. In this instance, regression may be identified if the number of auto-antibodies decreases in a later-obtained sample relative to an earlier obtained sample. The number of auto-antibodies may decrease by at least 1, at least 2, at least 3, at least 4, at least 5, at least 6, at least 7, at least 8, at least 9, or at least 10. Disease regression may be identified if level of any given auto-antibody decreases by at least 10%, at least 20%, at least 25%, at least 30%, at least 35%, at least 40%, at least 50%, at least 60%, at least 70%, at least 80%, at least 90%, or at least 95%. The number of auto-antibodies with decreased levels may be at least 1, at least 2, at least 3, at least 4, at least 5, at least 6, at least 7, at least 8, at least 9, at least 10, at least 15, at least 20, at least 25, at least 30, or at least 35. Any combination of decreased number and increased level of auto-antibody may indicate disease regression. Disease progression or disease regression may be monitored by obtaining samples over any period of time and at any interval. Disease progression or disease regression may be monitored by obtaining samples over the course of at least 1 week, at least 2 weeks, at least 3 weeks, at least 4 weeks, at least 5 weeks, at least 6 weeks, at least 7 weeks, at least 2 months, at least 3 months, at least 4 months, at least 5 months, at least 6 months, at least 1 year, at least 2 years, at least 3 years, at least 4 years, at least 5 years, at least 10 years, or over the lifetime of the patient. Disease progression or disease regression may be monitored by obtaining samples at least monthly, bi-monthly, once a quarter year, twice a year, or yearly. The samples need not be obtained at strict intervals.

In another embodiment is a method of prognosis of an auto-immune disorder of a patient. The autoimmune disorder may be any one of systemic lupus erythematosus, insulin dependent diabetes mellitus, inflammatory bowel disease (including Crohn's disease, ulcerative colitis, and Celiac's disease), multiple sclerosis, psoriasis, autoimmune thyroiditis, rheumatoid arthritis, glomerulonephritis, idiopathic inflammatory myositis, Sjogren's syndrome, vasculitis, dermatomyositis, polymyositis, inclusion body myositis, and sarcoidosis. Presence or absence of auto-antibodies is identified in a sample of the patient. Samples include any biological fluid or tissue, such as whole blood, saliva, urine, synovial fluid, bone marrow, cerebrospinal fluid, nasal secretions, sputum, amniotic fluid, bronchoalveolar lavage fluid, peripheral blood mononuclear cells, total white blood cells, lymph node cells, spleen cells, tonsil cells, or skin. The samples may be obtained by any of the well known means in the art.

The auto-antibodies may bind to any of the auto-antigens listed in Table 2, or Table 4, or Table 5, or Table 9. The auto-antigens may be all the auto-antigens listed in Table 2, or all the auto-antigens listed in Table 4, or all the auto-antigens listed in Table 5, or all the auto-antigens listed in Table 9. If the auto-antigens are a subset of the auto-antigens listed in any one of Tables 2, 4, 5, or 9 the auto-antigens may be (a) Myxovirus (influenza virus) resistance 1, interferon-inducible protein p78; (b) surfeit 5, transcript variant c; (c) proteasome (prosome, macropain) activator subunit 3 (PA28 gamma; Ki) transc; (d) retinoic acid receptor, alpha; (e) Heat shock 10 kDa protein 1 (chaperonin 10); (f) tropomyosin 3; (g) pleckstrin homology-like domain, family A, member 1; (h) cytoskeleton-associated protein 1; (i) Sjogren syndrome antigen A2 (60 kDa, ribonucleoprotein auto-antigen SS-A/Ro); (j) NADH dehydrogenase (ubiquinone) 1, alpha/beta subcomplex 1, 8 kDa; (k) NudE nuclear distribution gene E homolog 1 (*A. nidulans*); (l) MutL homolog 1, colon cancer, nonpolyposis type 2 (*E. coli*); (m) leucine rich repeat (in FLII) interacting protein 2; (n) tropomyosin 1 (alpha); (o) spastic paraplegia 20, spartin (Troyer syndrome); (p) preimplantation protein, transcript variant 1; (r) mitochondrial ribosomal protein L45; and (s) fumarate hydratase. The auto-antigens may be those highlighted in gray in Table 2. The auto-antigens may be those in bold in Table 2. The auto-antigens may be (a) Myxovirus (influenza virus) resistance 1 and interferon-inducible protein p78; and (b) surfeit 5, transcript variant c. The auto-antigens may be (a) Myxovirus (influenza virus) resistance 1, interferon-inducible protein p78; (b) surfeit 5, transcript variant c; and (c) proteasome (prosome, macropain) activator subunit 3 (PA28 gamma; Ki) transc. The auto-antigens may be (a) Myxovirus (influenza virus) resistance 1, interferon-inducible protein p78; (b) surfeit 5, transcript variant c; (c) proteasome (prosome, macropain) activator subunit 3 (PA28 gamma; Ki) transc; and (d) retinoic acid receptor, alpha. The auto-antigens may be (a) Myxovirus (influenza virus) resistance 1, interferon-inducible protein p78; (b) surfeit 5, transcript variant c; (c) proteasome (prosome, macropain) activator subunit 3 (PA28 gamma; Ki) transc; (d) retinoic acid receptor, alpha; and (e) Heat shock 10 kDa protein 1 (chaperonin 10). The auto-antigens may be (a) Myxovirus (influenza virus) resistance 1, interferon-inducible protein p78; (b) surfeit 5, transcript variant c; (c) proteasome (prosome, macropain) activator subunit 3 (PA28 gamma; Ki) transc; (d) retinoic acid receptor, alpha; (e) Heat shock 10 kDa protein 1 (chaperonin 10); and (f) tropomyosin 3. The autoantigens may be any 1, 2, 3, 4, 5, 6, 7, 8, 9, 10, 11, 12, 13, 14, 15, or 16 of PSME3, TPM3, RARα, FH, RPLP1, SSA2, HSPCA, PYCR1, CKAP1, SPG20, RAC1, LDHB, OSBPL9, MSN, PHLDA1, and PRE13. The autoantigens may be any 1, 2, 3, 4, 5, 6, 7, 8, 9, 10, 11, 12, 13, 14, 15, 16, or 17 of PSME3, TPM3, RARα, FH, RPLP1, SSA2, HSPCA, PYCR1, CKAP1, SPG20, RAC1, LDHB, OSBPL9, MSN, PHLDA1, PRE13, and HAGHL. The autoantigens may be any 1, 2, 3, 4, 5, 6, 7, 8, 9, 10, 11, 12, 13, 14, 15, 16, 17, 18, 19, 20, 21, 22, 23, or 24 of ankyrin repeat domain 13; ATP synthase, H+ transporting, mitochondrial F1 complex, beta polypeptide; chromosome 7 open reading frame 22; hypothetical protein DJ1042K10.2; eukaryotic translation elongation factor 1 gamma; fumarate hydratase; hepatocellular carcinoma-associated antigen 127; isopentenyl-diphosphate delta isomerase; macrophage migration inhibitory factor (glycosylation-inhibiting factor); mitochondrial ribosomal protein L45; moesin; oxysterol binding protein-like 9, transcript variant 1; protein phosphatase 1, regulatory (inhibitor) subunit 2 pseudogene 9; proteasome (prosome, macropain) activator subunit 3 (PA28 gamma; Ki), transc; ras-related C3 botulinum toxin substrate 1 (rho family, small GTP binding protein; RIO kinase 2 (yeast); ribosomal protein, large, P1; Sjogren syndrome antigen A2 (60 kDa, ribonucleoprotein autoantigen SS-A/Ro); synovial sarcoma, X breakpoint 2, transcript variant 2; serine/threonine kinase 16; TBC1 domain family, member 2; tudor and KH domain containing protein; target of myb1 (chicken); and/or urridine monophosphate kinase. The autoantigens may be any 1, 2, 3, 4, 5, 6, 7, 8, 9, 10, 11, 12, or 13 of ankyrin repeat domain 13; ATP synthase, H+ transporting, mitochondrial F1 complex, beta polypeptide; fumarate hydratase; moesin; oxysterol binding protein-like 9, transcript variant 1; proteasome (prosome, macropain) activator subunit 3 (PA28 gamma; Ki), transc; ribosomal protein, large, P1; Sjogren syndrome antigen A2 (60 kDa, ribonucleoprotein autoantigen SS-A/Ro); synovial sarcoma, X breakpoint 2, transcript variant 2; serine/threonine kinase 16; TBC1 domain family, member 2; tudor and KH domain containing protein; and/or target of myb1 (chicken). The autoantigens may be any 1, 2, 3, 4, 5, 6, or 7 of fumarate hydratase; proteasome (prosome, macropain) activator subunit 3 (PA28 gamma; Ki), transc; ribosomal protein, large, P1; Sjogren syndrome antigen A2 (6010a, ribonucleoprotein autoantigen SS-A/Ro); pyrroline-5-carboxylate reductase 1, transcript variant 1; retinoic acid receptor, alpha; and/or tropomyosin 3. The autoantigens may be any 1, 2, 3, or 4 of fumarate hydratase; proteasome (prosome, macropain) activator subunit 3 (PA28 gamma; Ki), trans; ribosomal protein, large, P1; and Sjorgren syndrome antigen A2 (60 kDa, ribonucleoprotein autoantigen SS-A/Ro). The autoantigens may be any 1, 2, or 3 of fumarate hydratase; protcasome (prosome, macropain) activator subunit 3 (PA28 gamma; Ki), trans; and ribosomal protein, large, P1. The autoantigens may be a member of the RA(X)R families and fumarate hydratase. The autoantigens may be any 1, 2, or 3 of proteasome (prosome, macropain) activator subunit 3 (PA28 gamma; Ki), transc; pyrroline-5-carboxylate reductase 1, transcript variant 1; and retinoic acid receptor, alpha. The autoantigens may be any 1, 2, 3, 4, 5, 6, 7, or 8 of fumarate hydratase; proteasome (prosome, macropain) activator subunit 3 (PA28 gamma; Ki), transc; ribosomal protein, large, P1; Sjogren syndrome antigen A2 (60 kDa, ribonucleoprotein autoantigen SS-A/Ro); lactate dehydrogenase B; pyrroline-5-carboxylate reductase 1, transcript variant 1; retinoic acid receptor, alpha; and tropomyosin. The autoantigens may be any 1, 2, 3, 4, 5, or 6 of proteasome (prosome, macropain) activator subunit 3 (PA28 gamma; Ki), transe; Sjogren syndrome antigen A2 (60 kDa, ribonucleoprotein autoantigen SS-A/Ro); cytoskeleton-associated protein 1; pyrroline-5-carboxylate reductase 1, transcript variant 1; retinoic acid receptor, alpha; and tropomyosin. The autoantigens may any subset of at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, or at least 30 shown in Table 9. The autoantigen may be one or more RA(X)R family member. The RA(X)R family member may be RARα, RARβ, RARγ, RXRα, RXRβ, RXRγ, or any isoform thereof. The RA(X)R family member may be RARα. The autoantigens may include an RA(X)R family member and any other 1, 2, 3, 4, 5, 6, 7, 8, 9, 10, 11, 12, 13, 14, 15, 16, 17, 18, 19, 20, 25, 30, or 35 autoantigens discussed above. The auto-antigens may be any at least 2, at least 3, at least 4, at least 5, at least 6, at least 7, at least 8, at least 9 at least 10, at least 11, at least 12, at least 13, at least 14, at least 15, at least 20, at least 25, at least 30, at least 35, at least 40, or at least 45 of those listed in Tables 2, 4, and/or 5 and/or 9. The autoantibodies to the autoantigens may be detected with one or more upregulated PD markers. The upregulated PD markers may be any one or more of RSAD2, HERC5, IRF7, MARCKS, LY6E, RAB8B, LILRA5, IFIT3, OAS1, IFIT1, EIF2AK2, G1P3, MX1, OAS3, STAT2, MX2, IRF2, FCHO2, IFI44, IFI44L, IL6ST, and G1P2. The upregulated PD markers may be any one or more of RSAD2, HERC5, IRF7, MARCKS, LY6E, RAB8B, LILRA5, IFIT3, OAS1, IFIT1, EIF2AK2, G1P3, MX1, OAS3, STAT2, MX2, IRF2, FCHO2, IFI44, IFI44L, IL6ST, and G1P2. The upregulated PD markers may be any one or more of RSAD2, HERC5, Ly6E, IFIT3, OAS1, G1P3, MX1, OAS3, and IFI44. The upregulated PD markers may be any one or more of RTP4, RSAD2, HERC5, SIGLEC1, USP18, LY6E, ETV7, SERPING1, IFIT3, OAS1, HSXIAPAF1, G1P3, MX1, OAS3, IFI27, DNAPTP6, LAMP3, EPSTI1, IFI44, OAS2, IFIT2, and ISG15. The upregulated PD markers may be any one or more of RTP4, RSAD2, HERC5, SIGLEC1, USP18, LY6E, ETV7, SERPING1, IFIT3, OAS1, HSXIAPAF1, G1P3, MX1, OAS3, IFI27, DNAPTP6, LAMP3, EPSTI1, IFI44, OAS2, IFIT2, and ISG15. The upregulated PD markers may be any one or more of HSXIAPAF1 and G1P3. The upregulated PD markers may be any one or more of XAF1, IFI27, IFIT2, USP18, OAS1, OAS2, EPST11, LY6E, RSAD2, LAMP3, ISG15, SERPING1, ETV7, RTP4, IFI6, OAS3, SIGLEC1, IFIT3, DNAPTP6, MX1, HERC5, and IFI44.

Presence of the auto-antibodies may be detected by any means known in the art and as described above, e.g., protein arrays, immunoprecipitation, and pulldown assays. Presence and levels of the auto-antibodies prognoses the autoimmune disorder. The presence of elevated numbers of auto-antibodies may indicate poor prognosis for the patient. Elevated number of auto-antibodies may be at least 1, at least 2, at least 3, at least 4, at least 5, at least 6, at least 7, at least 8, at least 9, at least 10, at least 11, at least 12, at least 15, at least 20 auto-antibodies more in a patient having an autoimmune disorder relative to a control patient or in the patient having the autoimmune disorder relative to a sample obtained at an earlier date. The presence of elevated levels of auto-antibodies may indicate poor prognosis for the patient. Elevated levels of auto-antibodies may be at least a 10% increase, at least a 15% increase, at least a 20% increase, at least a 25% increase, at least a 30% increase, at least a 40% increase, at least a 50% increase, at least a 60% increase, at least a 70% increase, at least an 80% increase, at least a 90% increase, or at least a 100% increase in at least 1, at least 2 at least 3, at least 4, at least 5, at least 6, at least 7, at least 8, at least 9, at least 10, at least 12, at least 15, at least 20, or at least 25 auto-antibodies in the patient relative to a healthy control or in the autoimmune disorder patient at an earlier date. Poor prognosis may be indicated by any combination of increased number and level of auto-antibodies in the autoimmune disease patient.

The presence of decreased numbers of auto-antibodies may indicate good prognosis for the patient. Decreased number of auto-antibodies may be at least 1, at least 2, at least 3, at least 4, at least 5, at least 6, at least 7, at least 8, at least 9, at least 10, at least 11, at least 12, at least 15, at least 20 auto-antibodies fewer in a patient having an autoimmune disorder relative to a control patient or in the patient having the autoimmune disorder relative to a sample obtained at an earlier date. The presence of decreased levels of auto-antibodies may indicate good prognosis for the patient. Decreased levels of auto-antibodies may be at least a 10% decrease, at least a 15% decrease, at least a 20% decrease, at least a 25% decrease, at least a 30% decrease, at least a 40% decrease, at least a 50% decrease, at least a 60% decrease, at least a 70% decrease, at least an 80% decrease, at least a 90% decrease, or at least a 100% decrease in at least 1, at least 2 at least 3, at least 4, at least 5, at least 6, at least 7, at least 8, at least 9, at least 10, at least 12, at least 15, at least 20, or at least 25 auto-antibodies in the patient relative to a healthy control or in the autoimmune disorder patient at an earlier date. Good prognosis may be indicated by any combination of decreased number and level of auto-antibodies in the autoimmune disease patient.

Applicants provide a set of non-limiting embodiments to describe some of the aspects of the invention.

EMBODIMENTS

Embodiment 1

A method of treating a patient having a type I IFN or IFNα-related autoimmune disorder comprising:
administering an agent that binds to and modulates type I IFN or IFNα activity;
wherein the patient having the autoimmune disorder comprises auto-antibodies that bind at least any two auto-antigens of
  (a) Myxovirus (influenza virus) resistance 1, interferon-inducible protein p78;
  (b) surfeit 5, transcript variant c;
  (c) proteasome (posome, macropain) activator subunit 3 (PA28 gamma; Ki) transc;
  (d) retinoic acid receptor, alpha;
  (e) Heat shock 10 kDa protein 1 (chaperonin 10);
  (f) tropomyosin 3;
  (g) pleckstrin homology-like domain, family A, member 1;
  (h) cytoskeleton-associated protein 1;
  (i) Sjogren syndrome antigen A2 (60 kDa, ribonucleoprotein auto-antigen SS-A/Ro);
  (j) NADH dehydrogenase (ubiquinone) 1, alpha/beta subcomplex 1, 8 kDa;
  (k) NudE nuclear distribution gene E homolog 1 (*A. nidulans*);
  (l) MutL homolog 1, colon cancer, nonpolyposis type 2 (*E. coli*);
  (m) leucine rich repeat (in FLII) interacting protein 2;
  (n) tropomyosin 1 (alpha);
  (o) spastic paraplegia 20, spartin (Troyer syndrome);
  (p) preimplantation protein, transcript variant 1;
  (r) mitochondrial ribosomal protein L45; and
  (s) fumarate hydratase and
wherein the agent reduces number or levels of the auto-antibodies that bind the at least any two auto-antigens in the patient.

Embodiment 2

The method of embodiment 1 further comprising detecting reduction of the number or levels of the auto-antibodies that bind the at least any two auto-antigens in the patient.

Embodiment 3

The method of embodiment 1 wherein the patient further comprises a type I IFN or IFNα-inducible PD marker expression profile, said profile comprising up-regulated expression or activity of genes MX1, LY6E, IFI27, OAS1, IFIT1, IFI6, IFI44L, ISG15, LAMP3, OASL, RSAD2, and IFI44.

Embodiment 4

The method of embodiment 1 wherein the agent is a biologic agent.

Embodiment 5

The method of embodiment 4 wherein the agent is an antibody.

Embodiment 6

The method of embodiment 5 wherein the antibody is MEDI-545.

Embodiment 7

The method of embodiment 5 wherein the antibody is specific for one or more type I IFNs, but is not MEDI-545.

Embodiment 8

The method of embodiment 1 wherein administering the agent alleviates one or more symptom of the disorder.

Embodiment 9

The method of embodiment 5 wherein the antibody is administered at a dose between approximately 0.03 and 30 mg/kg.

Embodiment 10

The method of embodiment 9 wherein the antibody is administered at a dose between 0.03 and 3.0 mg/kg.

Embodiment 11

The method of embodiment 10 wherein the antibody is administered at a dose between 0.03 and 1 mg/kg.

Embodiment 12

The method of any one of embodiments 9-11 wherein levels of the auto-antibodies are reduced at least 10%.

Embodiment 13

The method of embodiment 12 wherein levels of the auto-antibodies are reduced at least 20%

Embodiment 14

The method of embodiment 12 wherein levels of the auto-antibodies are reduced at least 30%.

Embodiment 15

The method of embodiment 12 wherein levels of the auto-antibodies are reduced at least 50%.

Embodiment 16

The method of embodiment 1 wherein the autoimmune disorder is one of lupus, psoriasis, vasculitis, sarcoidosis, Sjogren's syndrome, or idiopathic inflammatory myositis.

Embodiment 17

The method of embodiment 16 wherein the autoimmune disorder is lupus.

Embodiment 18

The method of embodiment 16 wherein the autoimmune disorder is psoriasis.

Embodiment 19

The method of embodiment 1 wherein the type I IFN or IFNα-related autoimmune disorder is mediated by upregulated expression or activity of at least IFN subtypes 1, 2, 8, and 14.

Embodiment 20

The method of embodiment 3 wherein the type I IFN or IFNα-inducible PD marker expression profile is neutralized at least 10%.

Embodiment 21

The method of embodiment 20 wherein the type I IFN or IFNα-inducible PD marker expression profile is neutralized at least 20%.

Embodiment 22

The method of embodiment 21 wherein the type I IFN or IFNα-inducible PD marker expression profile is neutralized at least 30%.

Embodiment 23

The method of embodiment 22 wherein the type I IFN or IFNα-inducible PD marker expression profile is neutralized at least 50%.

Embodiment 24

The method of any one of embodiments 20-23 wherein levels of the auto-antibodies are reduced at least 10%.

Embodiment 25

The method of embodiment 24 wherein levels of the auto-antibodies are reduced at least 20%.

Embodiment 26

The method of embodiment 25 wherein levels of the auto-antibodies are reduced at least 30%.

Embodiment 27

The method of embodiment 26 wherein levels of the auto-antibodies are reduced at least 50%.

Embodiment 28

The method of embodiment 1 wherein the auto-antibodies bind at least any three of the auto-antigens.

Embodiment 29

The method of embodiment 28 wherein the auto-antibodies bind at least any four of the auto-antigens.

Embodiment 30

The method of embodiment 29 wherein the auto-antibodies bind at least any five of the auto-antigens.

Embodiment 31

A method of diagnosing a patient as having a type I IFN or IFNα-related autoimmune disorder comprising:

detecting presence or absence of auto-antibodies in a sample of a patient;
wherein the auto-antibodies bind at least any two auto-antigens of
(a) Myxovirus (influenza virus) resistance 1, interferon-inducible protein p78;
(b) surfeit 5, transcript variant c;
(c) proteasome (posome, macropain) activator subunit 3 (PA28 gamma; Ki) transc;
(d) retinoic acid receptor, alpha;
(e) Heat shock 10 kDa protein 1 (chaperonin 10);
(f) tropomyosin 3;
(g) pleckstrin homology-like domain, family A, member 1;
(h) cytoskeleton-associated protein 1;
(i) Sjogren syndrome antigen A2 (60 kDa, ribonucleoprotein auto-antigen SS-A/Ro);
(j) NADH dehydrogenase (ubiquinone) 1, alpha/beta subcomplex 1, 8 kDa;
(k) NudE nuclear distribution gene E homolog 1 (*A. nidulans*);
(l) MutL homolog 1, colon cancer, nonpolyposis type 2 (*E. coli*);
(m) leucine rich repeat (in FLIT) interacting protein 2;
(n) tropomyosin 1 (alpha);
(o) spastic paraplegia 20, spartin (Troyer syndrome);
(p) preimplantation protein, transcript variant 1;
(r) mitochondrial ribosomal protein L45; and
(s) fumarate hydratase
wherein detecting the presence of the auto-antibodies diagnoses the patient as having the autoimmune disorder.

Embodiment 32

The method of embodiment 31 wherein the auto-antibodies bind at least any three of the auto-antigens.

Embodiment 33

The method of embodiment 32 wherein the auto-antibodies bind at least any four of the auto-antigens.

Embodiment 34

The method of embodiment 33 wherein the auto-antibodies bind any at least five of the auto-antigens.

Embodiment 35

The method of embodiment 31 wherein the autoimmune disorder is one of lupus, psoriasis, vasculitis, sarcoidosis, Sjogren's syndrome, or idiopathic inflammatory myositis.

Embodiment 36

The method of embodiment 35 wherein the autoimmune disorder is lupus.

Embodiment 37

The method of embodiment 35 wherein the autoimmune disorder is psoriasis.

Embodiment 38

A method of monitoring autoimmune disorder progression of a patient receiving treatment with a therapeutic agent that binds to and modulates type I IFN or IFNα activity comprising:

identifying auto-antibodies in a first sample of a patient;
wherein the auto-antibodies bind at least any two auto-antigens of:
  (a) Myxovirus (influenza virus) resistance 1, interferon-inducible protein p78;
  (b) surfeit 5, transcript variant c;
  (c) proteasome (posome, macropain) activator subunit 3 (PA28 gamma; Ki) transc;
  (d) retinoic acid receptor, alpha;
  (e) Heat shock 10 kDa protein 1 (chaperonin 10);
  (f) tropomyosin 3;
  (g) pleckstrin homology-like domain, family A, member 1;
  (h) cytoskeleton-associated protein 1;
  (i) Sjogren syndrome antigen A2 (60 kDa, ribonucleoprotein auto-antigen SS-A/Ro);
  (j) NADH dehydrogenase (ubiquinone) 1, alpha/beta subcomplex 1, 8 kDa;
  (k) NudE nuclear distribution gene E homolog 1 (*A. nidulans*);
  (l) MutL homolog 1, colon cancer, nonpolyposis type 2 (*E. coli*);
  (m) leucine rich repeat (in FLII) interacting protein 2;
  (n) tropomyosin 1 (alpha);
  (o) spastic paraplegia 20, spartin (Troyer syndrome);
  (p) preimplantation protein, transcript variant 1;
  (r) mitochondrial ribosomal protein L45; and
  (s) fumarate hydratase
administering a therapeutic agent that binds to and modulates type I IFN or IFNα activity;
identifying auto-antibodies in a second sample from the patient; and
comparing the auto-antibodies in the first and second sample from the patient,
  wherein a variance in the auto-antibodies in the first and second sample indicates a level of efficacy of the therapeutic agent that binds to and modulates type I IFN or IFNα activity.

Embodiment 39

The method of embodiment 38 wherein the autoimmune disorder is one of lupus, psoriasis, vasculitis, sarcoidosis, Sjogren's syndrome, or idiopathic inflammatory myositis.

Embodiment 40

The method of embodiment 39 wherein the autoimmune disorder is lupus.

Embodiment 41

The method of embodiment 39 wherein the autoimmune disorder is psoriasis.

Embodiment 42

The method of embodiment 38 wherein the variance is fewer auto-antibodies in the second sample relative to the first sample.

Embodiment 43

The method of embodiment 38 wherein the variance is lower levels of auto-antibodies in the second sample relative to the second sample.

Embodiment 44

The method of embodiment 38 wherein the first and the second sample are serum or whole blood.

Embodiment 45

The method of embodiment 38 wherein the therapeutic agent is a biologic.

Embodiment 46

The method of embodiment 45 wherein the biologic is an antibody.

Embodiment 47

The method of embodiment 46 wherein the antibody is MEDI-545.

Embodiment 48

The method of embodiment 38 wherein the first sample is obtained from the patient prior to a first exposure to the therapeutic agent.

Embodiment 49

The method of embodiment 38 wherein the first sample is obtained from the patient following a first exposure to the therapeutic.

Embodiment 50

A method of prognosing a patient having a type I IFN or IFNα-mediated auto-immune disorder comprising:

identifying presence or absence of auto-antibodies in a sample of a patient;

wherein the auto-antibodies bind auto-antigens selected from the grouop consisting of (a) Myxovirus (influenza virus) resistance 1, interferon-inducible protein p78;

(b) surfeit 5, transcript variant c;

(c) proteasome (posome, macropain) activator subunit 3 (PA28 gamma; Ki) transc;

(d) retinoic acid receptor, alpha;

(e) Heat shock 10 kDa protein 1 (chaperonin 10);

(f) tropomyosin 3;

(g) pleckstrin homology-like domain, family A, member 1;

(h) cytoskeleton-associated protein 1;

(i) Sjogren syndrome antigen A2 (60 kDa, ribonucleoprotein auto-antigen SS-A/Ro);

(j) NADH dehydrogenase (ubiquinone) 1, alpha/beta subcomplex 1, 8 kDa;

(k) NudE nuclear distribution gene E homolog 1 (*A. nidulans*);

(l) MutL homolog 1, colon cancer, nonpolyposis type 2 (*E. coli*);

(m) leucine rich repeat (in FLIT) interacting protein 2;

(n) tropomyosin 1 (alpha);

(o) spastic paraplegia 20, spartin (Troyer syndrome);

(p) preimplantation protein, transcript variant 1;

(r) mitochondrial ribosomal protein L45;

(s) Lin-28 homolog (*C. elegans*);

(t) heat shock 90 kDa protein 1, alpha;

(u) dom-3 homolog Z (*C. elegans*);

(v) dynein, cytoplasmic, light intermediate polypeptide 2;
(w) Ras-related C3 botulinum toxin substrate 1 (rho family, small GTP binding protein);
(x) synovial sarcoma, X breakpoint 2, transcript variant 2;
(y) moesin;
(z) homer homolog (Drosophila), transcript variant 1;
(aa) GCN5 general control of amino-acid synthesis 5-like 2 (yeast);
(bb) eukaryotic translation elongation factor 1 gamma;
(cc) eukaryotic translation elongation factor 1, delta;
(dd) DNA-damage-inducible transcript 3;
(ee) CCAAT/enhancer binding protein (C/EBP) gamma; and
(ff) fumarate hydratase
wherein presence and levels of the auto-antibodies in the sample prognoses the autoimmune disorder.

Embodiment 51

The method of embodiment 50 wherein presence of at least two auto-antibodies is identified.

Embodiment 52

The method of embodiment 51 wherein presence of at least three auto-antibodies is identified.

Embodiment 53

The method of embodiment 52 wherein presence of at least five auto-antibodies is identified.

Embodiment 54

A method of treating a patient having a type I IFN or IFNα-related autoimmune disorder comprising:
administering an agent that binds to and modulates type I IFN or IFNα activity;
wherein the patient having the autoimmune disorder comprises auto-antibodies that bind to at least a retinoic acid and retinoid X receptor (RA(X)R), and
wherein the agent reduces number or levels of the auto-antibodies that bind the RA(X)R.

Embodiment 55

The method of embodiment 54 wherein the RA(X)R is RARα.

Embodiment 56

The method of embodiment 54 wherein the RA(X)R is RARγ.

Embodiment 57

The method of embodiment 54 wherein the RA(X)R is RXRα.

Embodiment 58

The method of embodiment 54 wherein the RA(X)R is RXRβ.

Embodiment 59

The method of any one of embodiments 54-58 wherein the patient further comprises auto-antibodies that bind to any one or more of the following auto-antigens:
(a) Myxovirus (influenza virus) resistance 1, interferon-inducible protein p78;
(b) surfeit 5, transcript variant c;
(c) proteasome (posome, macropain) activator subunit 3 (PA28 gamma; Ki) transc;
(d) retinoic acid receptor, alpha;
(e) Heat shock 10 kDa protein 1 (chaperonin 10);
(f) tropomyosin 3;
(g) pleckstrin homology-like domain, family A, member 1;
(h) cytoskeleton-associated protein 1;
(i) Sjogren syndrome antigen A2 (60 kDa, ribonucleoprotein auto-antigen SS-A/Ro);
(j) NADH dehydrogenase (ubiquinone) 1, alpha/beta subcomplex 1, 8 kDa;
(k) NudE nuclear distribution gene E homolog 1 (*A. nidulans*);
(l) MutL homolog 1, colon cancer, nonpolyposis type 2 (*E. coli*);
(m) leucine rich repeat (in FLII) interacting protein 2;
(n) tropomyosin 1 (alpha);
(o) spastic paraplegia 20, spartin (Troyer syndrome);
(p) preimplantation protein, transcript variant 1;
(r) mitochondrial ribosomal protein L45;
(s) fumarate hydratase (FH);
(t) ribosomal protein, large, P1 (RPLP1);
(u) heat shock 90 kDa protein 1, alpha (HSPCA);
(v) pyrroline-5-carboxylate reductase 1, transcript variant (PYCR1);
(w) ras-related C3 botulinum toxin stubstrate 1, rho family (RAC1);
(x) lactate dehydrogenase B (LDHB);
(y) oxysterol binding protein-like 9, transcript variant (OSBPL9);
(z) moesin (MSN);
(aa) pleckstrin homology-like domain, family A, member 1 (PHLDA1); or
(bb) hydroxyacyl glutathion hydrolase-like (HAGHL);
wherein the agent reduces the number or levels of the auto-antibodies that bind to any one or more of the auto-antigens of (a)-(bb).

Embodiment 60

The method of any of embodiments 54-58 wherein the patient further comprises a type I IFN or IFNα-inducible PD marker expression profile.

Embodiment 61

The method of embodiment 59 wherein the patient further comprises a type I IFN or IFNα-inducible PD marker expression profile.

Embodiment 62

The method of any of embodiments 54-58 wherein the agent is a biologic agent.

Embodiment 63

The method of embodiment 59 wherein the agent is a biologic agent.

Embodiment 64

The method of embodiment 62 wherein the agent is an antibody.

Embodiment 65

The method of embodiment 63 wherein the agent is an antibody.

Embodiment 66

The method of embodiment 64 wherein the antibody is MEDI-545.

Embodiment 67

The method of embodiment 65 wherein the antibody is MEDI-545.

Embodiment 68

The method of embodiment 64 wherein the antibody is specific for one or more type I IFNs, but is not MEDI-545.

Embodiment 69

The method of embodiment 65 wherein the antibody is specific for one or more type I IFNs, but is not MEDI-545.

Embodiment 70

The method of any one of embodiments 54-58 wherein administering the agent alleviates one or more symptom of the disorder.

Embodiment 71

The method of embodiment 59 wherein administering the agent alleviates one or more symptom of the disorder.

Embodiment 72

The method of 64 wherein the antibody is administered at a dose between approximately 0.03 to 30 mg/kg.

Embodiment 73

The method of embodiment 65 wherein the antibody is administered at a dose between approximately 0.03 to 30 mg/kg.

Embodiment 74

The method of embodiment 72 wherein the antibody is administered at a dose between approximately 0.03 to 3.0 mg/kg.

Embodiment 75

The method of embodiment 73 wherein the antibody is administered at a dose between approximately 0.03 to 3.0 mg/kg.

Embodiment 76

The method of embodiment 74 wherein levels of the autoantibodies are reduced at least 10%.

Embodiment 77

The method of embodiment 75 wherein levels of the autoantibodies are reduced at least 10%.

Embodiment 78

The method of embodiment 54 wherein the autoimmune disorder is one of lupus, psoriasis, vasculitis, sarcoidosis, Sjogren's syndrome, or idiopathic inflammatory myositis.

Embodiment 79

The method of embodiment 78 wherein the autoimmune disorder is lupus.

Embodiment 80

The method of embodiment 78 wherein the autoimmune disorder is psoriasis.

Embodiment 81

The method of embodiment 54 wherein the type I IFN or IFNα-related autoimmune disorder is mediated by upregulated expression or activity of at least IFN subtypes 1, 2, 8, and 14.

Embodiment 82

The method of embodiment 60 wherein the type I IFN or IFNα-inducible PD marker expression profile is neutralized at least 10%.

Embodiment 83

The method of embodiment 61 wherein the type I IFN or IFNα-inducible PD marker expression profile is neutralized at least 10%.

Embodiment 84

The method of embodiment 82 wherein the type I IFN or IFNα-inducible PD marker expression profile is neutralized at least 20%.

Embodiment 85

The method of embodiment 83 wherein the type I IFN or IFNα-inducible PD marker expression profile is neutralized at least 20%.

Embodiment 86

The method of embodiment 84 wherein the type I IFN or IFNα-inducible PD marker expression profile is neutralized at least 30%.

Embodiment 87

The method of embodiment 85 wherein the type I IFN or IFNα-inducible PD marker expression profile is neutralized at least 30%.

Embodiment 88

The method of embodiment 86 wherein the type I IFN or IFNα-inducible PD marker expression profile is neutralized at least 50%.

Embodiment 89

The method of embodiment 87 wherein the type I IFN or IFNα-inducible PD marker expression profile is neutralized at least 50%.

Embodiment 90

A method of diagnosing a patient as having a type I IFN or IFNα-related autoimmune disorder comprising:
  detecting presence or absence of auto-antibodies in a sample of a patient;
    wherein the auto-antibodies bind at least a retinoic acid and retinoid X receptor (RA(X)R).

Embodiment 91

The method of embodiment 90 wherein the RA(X)R is RARα

Embodiment 92

The method of embodiment 90 wherein the RA(X)R is RARγ.

Embodiment 93

The method of embodiment 90 wherein the RA(X)R is RXRα.

Embodiment 94

The method of embodiment 90 wherein the RA(X)R is RXRβ.

Embodiment 95

The method of any one of embodiments 90-94 further comprising detecting presence or absence of auto-antibodies to one or more of the following auto-antigens:
  (a) Myxovirus (influenza virus) resistance 1, interferon-inducible protein p78;
  (b) surfeit 5, transcript variant c;
  (c) proteasome (posome, macropain) activator subunit 3 (PA28 gamma; Ki) tram;
  (d) retinoic acid receptor, alpha;
  (e) Heat shock 10 kDa protein 1 (chaperonin 10);
  (f) tropomyosin 3;
  (g) pleckstrin homology-like domain, family A, member 1;
  (h) cytoskeleton-associated protein 1;
  (i) Sjogren syndrome antigen A2 (60 kDa, ribonucleoprotein auto-antigen SS-A/Ro);
  (j) NADH dehydrogenase (ubiquinone) 1, alpha/beta subcomplex 1, 8 kDa;
  (k) NudE nuclear distribution gene E homolog 1 (*A. nidulans*);
  (l) MutL homolog 1, colon cancer, nonpolyposis type 2 (*E. coli*);
  (m) leucine rich repeat (in FLIT) interacting protein 2;
  (n) tropomyosin 1 (alpha);
  (o) spastic paraplegia 20, spartin (Troyer syndrome);
  (p) preimplantation protein, transcript variant 1;
  (r) mitochondrial ribosomal protein L45;
  (s) fumarate hydratase (FH);
  (t) ribosomal protein, large, P1 (RPLP1);
  (u) heat shock 90 kDa protein 1, alpha (HSPCA);
  (v) pyrroline-5-carboxylate reductase 1, transcript variant (PYCR1);
  (w) ras-related C3 botulinum toxin stubstrate 1, rho family (RAC1);
  (x) lactate dehydrogenase B (LDHB);
  (y) oxysterol binding protein-like 9, transcript variant (OSBPL9);
  (z) moesin (MSN);
  (aa) pleckstrin homology-like domain, family A, member 1 (PHLDA1); or
  (bb) hydroxyacyl glutathion hydrolase-like (HAGHL).

Embodiment 96

The method of any of embodiments 90-94 wherein the autoimmune disorder is one of lupus, psoriasis, vasculitis, sarcoidosis, Sjogren's syndrome, or idiopathic inflammatory myositis.

Embodiment 97

The method of embodiment 95 wherein the autoimmune disorder is one of lupus, psoriasis, vasculitis, sarcoidosis, Sjogren's syndrome, or idiopathic inflammatory myositis.

Embodiment 98

The method of embodiment 96 wherein the autoimmune disorder is lupus.

Embodiment 99

The method of embodiment 97 wherein the autoimmune disorder is lupus.

Embodiment 100

The method of embodiment 96 wherein the autoimmune disorder is psoriasis.

Embodiment 101

The method of embodiment 97 wherein the autoimmune disorder is psoriasis.

Embodiment 102

A method of monitoring autoimmune disorder progression of a patient receiving treatment with a therapeutic agent that binds to and modulates type I IFN or IFNα activity comprising:
  identifying auto-antibodies in a first sample of a patient;
    wherein the auto-antibodies bind to at least a retinoic acid and retinoid X receptor (RA(X)R);
  administering a therapeutic agent that binds to and modulates type I IFN or IFNα activity;
  identifying the auto-antibodies in a second sample from the patient; and
  comparing the auto-antibodies in the first and second sample from the patient, wherein a variance in the auto-antibodies in the first and second sample indicates a level of efficacy of the therapeutic agent that binds to and modulates type I IFN or IFNα activity.

Embodiment 103

The method of embodiment 102 wherein the RA(X)R is RARα.

Embodiment 104

The method of embodiment 102 wherein the RA(X)R is RARγ.

Embodiment 105

The method of embodiment 102 wherein the RA(X)R is RXRα.

Embodiment 106

The method of embodiment 102 wherein the RA(X)R is RXRβ.

Embodiment 107

The method of any one of embodiments 102-106 wherein the patient further comprises auto-antibodies that bind to one or more of the following auto-antigens:
- (a) Myxovirus (influenza virus) resistance 1, interferon-inducible protein p78;
- (b) surfeit 5, transcript variant c;
- (c) proteasome (posome, macropain) activator subunit 3 (PA28 gamma; Ki) transc;
- (d) retinoic acid receptor, alpha;
- (e) Heat shock 10 kDa protein 1 (chaperonin 10);
- (f) tropomyosin 3;
- (g) pleckstrin homology-like domain, family A, member 1;
- (h) cytoskeleton-associated protein 1;
- (i) Sjogren syndrome antigen A2 (60 kDa, ribonucleoprotein auto-antigen SS-A/Ro);
- (j) NADH dehydrogenase (ubiquinone) 1, alpha/beta subcomplex 1, 8 kDa;
- (k) NudE nuclear distribution gene E homolog 1 (*A. nidulans*);
- (l) MULL homolog 1, colon cancer, nonpolyposis type 2 (*E. coli*);
- (m) leucine rich repeat (in FLIT) interacting protein 2;
- (n) tropomyosin 1 (alpha);
- (o) spastic paraplegia 20, spartin (Troyer syndrome);
- (p) preimplantation protein, transcript variant 1;
- (r) mitochondrial ribosomal protein L45;
- (s) fumarate hydratase (FH);
- (t) ribosomal protein, large, P1 (RPLP1);
- (u) heat shock 90 kDa protein 1, alpha (HSPCA);
- (v) pyrroline-5-carboxylate reductase 1, transcript variant (PYCR1);
- (w) ras-related C3 botulinum toxin stubstrate 1, rho family (RAC1);
- (x) lactate dehydrogenase B (LDHB);
- (y) oxysterol binding protein-like 9, transcript variant (OSBPL9);
- (z) moesin (MSN);
- (aa) pleckstrin homology-like domain, family A, member 1 (PHLDA1); or
- (bb) hydroxyacyl glutathion hydrolase-like (HAGHL).

Embodiment 108

The method of any one of embodiments 102-106 wherein the autoimmune disorder is one of lupus, psoriasis, vasculitis, sarcoidosis, Sjogren's syndrome, or idiopathic inflammatory myositis.

Embodiment 109

The method of embodiment 107 wherein the autoimmune disorder is one of lupus, psoriasis, vasculitis, sarcoidosis, Sjogren's syndrome, or idiopathic inflammatory myositis.

Embodiment 110

The method of embodiment 108 wherein the autoimmune disorder is lupus.

Embodiment 111

The method of embodiment 109 wherein the autoimmune disorder is lupus.

Embodiment 112

The method of embodiment 108 wherein the autoimmune disorder is psoriasis.

Embodiment 113

The method of embodiment 109 wherein the autoimmune disorder is psoriasis.

Embodiment 114

The method of any one of embodiments 102-106 wherein the variance is fewer auto-antibodies in the second sample relative to the first sample.

Embodiment 115

The method of embodiment 107 wherein the variance is fewer auto-antibodies in the second sample relative to the first sample.

Embodiment 116

The method of any one of embodiments 102-106 wherein the variance is lower levels of auto-antibodies in the second sample relative to the first sample.

Embodiment 117

The method of embodiment 107 wherein the variance is lower levels of auto-antibodies in the second sample relative to the first sample.

Embodiment 118

The method of embodiment 102 or 107 wherein the first and the second sample are serum or whole blood.

Embodiment 119

The method of embodiment 102 or 107 wherein the therapeutic agent is a biologic agent.

Embodiment 120

The method of embodiment 119 wherein the biologic agent is an antibody.

Embodiment 121

The method of embodiment 120 wherein the antibody is MEDI-545.

Embodiment 122

The method of embodiment 102 or 107 wherein the first sample is obtained from the patient prior to a first exposure to the therapeutic agent.

Embodiment 123

The method of embodiment 102 or 107 wherein the first sample is obtained from the patient following a first exposure to the therapeutic.

Embodiment 124

A method of prognosing a patient having a type I IFN or IFNα-mediated autoimmune disorder comprising:
identifying presence or absence of auto-antibodies in a sample of a patient;
wherein the auto-antibodies bind at least a retinoic acid and retinoid X receptor (RA(X)R) in a sample of the patient;
wherein presence and levels of the auto-antibodies in the sample prognoses the autoimmune disorder.

Embodiment 125

The method of embodiment 124 wherein the RA(X)R is RARα.

Embodiment 126

The method of embodiment 124 wherein the RA(X)R is RARγ.

Embodiment 127

The method of embodiment 124 wherein the RA(X)R is RXRα.

Embodiment 128

The method of embodiment 124 wherein the RA(X)R is RXRβ.

Embodiment 129

The method of any one of embodiments 124-128 wherein the patient further comprises auto-antibodies that bind to one or more of the following auto-antigens:
(a) Myxovirus (influenza virus) resistance 1, interferon-inducible protein p78;
(b) surfeit 5, transcript variant c;
(c) proteasome (posome, macropain) activator subunit 3 (PA28 gamma; Ki) transc;
(d) retinoic acid receptor, alpha;
(e) Heat shock 10 kDa protein 1 (chaperonin 10);
(f) tropomyosin 3;
(g) pleckstrin homology-like domain, family A, member 1;
(h) cytoskeleton-associated protein 1;
(i) Sjogren syndrome antigen A2 (60 kDa, ribonucleoprotein auto-antigen SS-A/Ito);
(j) NADH dehydrogenase (ubiquinone) 1, alpha/beta subcomplex 1, 8 kDa;
(k) NudE nuclear distribution gene E homolog 1 (*A. nidulans*);
(l) MutL homolog 1, colon cancer, nonpolyposis type 2 (*E. coli*);
(m) leucine rich repeat (in FLII) interacting protein 2;
(n) tropomyosin 1 (alpha);
(o) spastic paraplegia 20, spartin (Troyer syndrome);
(p) preimplantation protein, transcript variant 1;
(r) mitochondrial ribosomal protein L45;
(s) fumarate hydratase (FH);
(t) ribosomal protein, large, P1 (RPLP1);
(u) heat shock 90 kDa protein 1, alpha (HSPCA);
(v) pyrroline-5-carboxylate reductase 1, transcript variant (PYCR1);
(w) ras-related C3 botulinum toxin stubstrate 1, rho family (RAC1);
(x) lactate dehydrogenase B (LDHB);
(y) oxysterol binding protein-like 9, transcript variant (OSBPL9);
(z) moesin (MSN);
(aa) pleckstrin homology-like domain, family A, member 1 (PHLDA1); and
(bb) hydroxyacyl glutathion hydrolase-like (HAGHL).

Embodiment 130

The method of any one of embodiments 124-128 wherein the autoimmune disorder is one of lupus, psoriasis, vasculitis, sarcoidosis, Sjogren's syndrome, or idiopathic inflammatory myositis.

Embodiment 131

The method of embodiment 129 wherein the autoimmune disorder is one of lupus, psoriasis, vasculitis, sarcoidosis, Sjogren's syndrome, or idiopathic inflammatory myositis.

Embodiment 132

The method of embodiment 130 wherein the autoimmune disorder is lupus.

Embodiment 133

The method of embodiment 131 wherein the autoimmune disorder is lupus.

Embodiment 134

The method of embodiment 130 wherein the autoimmune disorder is psoriasis.

Embodiment 135

The method of embodiment 131 wherein the autoimmune disorder is psoriasis.

Embodiment 136

The method of any one of embodiments 90-94 further comprising identifying the patient as a candidate for therapy with an agent that modulates type I IFN or IFNα activity.

This application claims the benefit of priority of U.S. Provisional Application Ser. No. 60/924,219 filed May 3, 2007, U.S. Provisional Application Ser. No. 60/924,584 filed May 21, 2007, U.S. Provisional Application Ser. No. 60/960,187 filed Sep. 19, 2007, U.S. Provisional Application Ser. No. 60/996,176 filed Nov. 5, 2007, and PCT application PCT/US2007/024947 filed Dec. 6, 2007 herein incorporated by reference for all purposes. This application also claims the benefit of priority of U.S. Provisional Application Ser. No. 60/924,220 filed May 3, 2007, U.S. Provisional Application Ser. No. 60/996,219 filed Nov. 6, 2007, and U.S. Provisional Application Ser. No. 60/996,820 filed Dec. 6, 2007, herein incorporated by reference for all purposes. This application further claims the benefit of priority of U.S. Provisional Application Ser. No. 60/996,174 filed Nov. 5, 2007, and PCT application PCT/US2007/024941 filed Dec. 6, 2007, herein incorporated by reference for all purposes. This application further claims the benefit of priority of U.S. Provisional Application Ser. No. 61/006,963 filed Feb. 8, 2008, herein incorporated by reference for all purposes.

All publications, patents and patent applications mentioned in this specification are herein incorporated by reference into the specification to the same extent as if each individual publication, patent or patent application was specifically and individually indicated to be incorporated herein by reference.

The set of examples that follow are provided for the purpose of illustration only and the invention should in no way be construed as being limited to these examples.

EXAMPLES

Example 1

Identification of Auto-Antibodies in Pooled Serum Samples of SLE Patients

Figure 2:
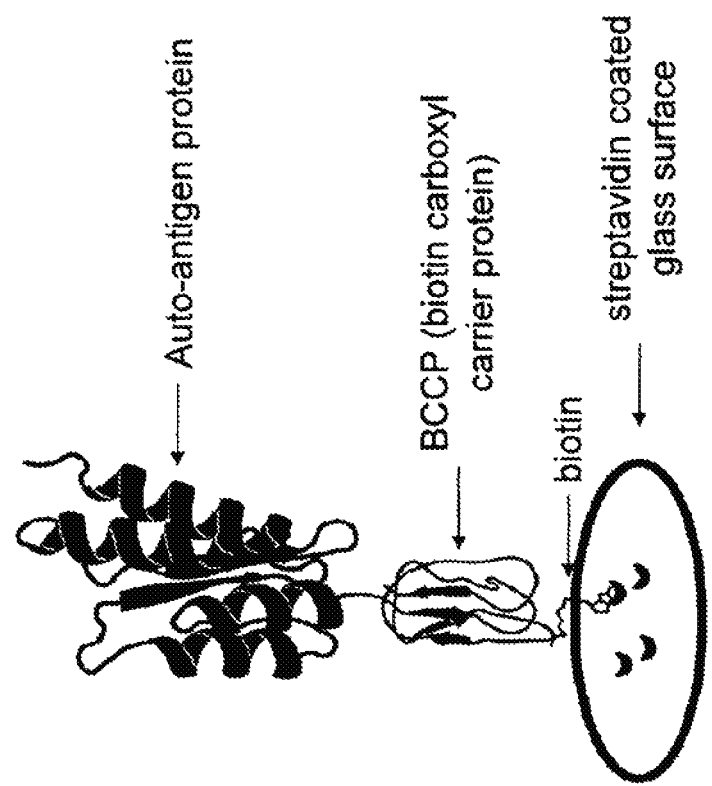
FIG. 2: Architecture of proteins as spotted on auto-antigen arrays.

Serum of normal individuals and of individuals diagnosed with SLE was examined for auto-antibodies using an auto-antigen array. The auto-antigen arrays were spotted with 330 known cancer auto-antigens, each auto-antigen spotted in quadruplicate, identified from the Cancer Immunome Database maintained by the Ludwig Institute for Cancer Research. Auto-antigens spotted on the array project into an aqueous environment and orient away from the surface of the glass chips, exposing them for binding by auto-antibodies. See FIGS. 1 and 2, which provide a schematic illustration of auto-antigens on an array and the architecture of a single auto-antigen attached to an array, respectively.

Figure 3:
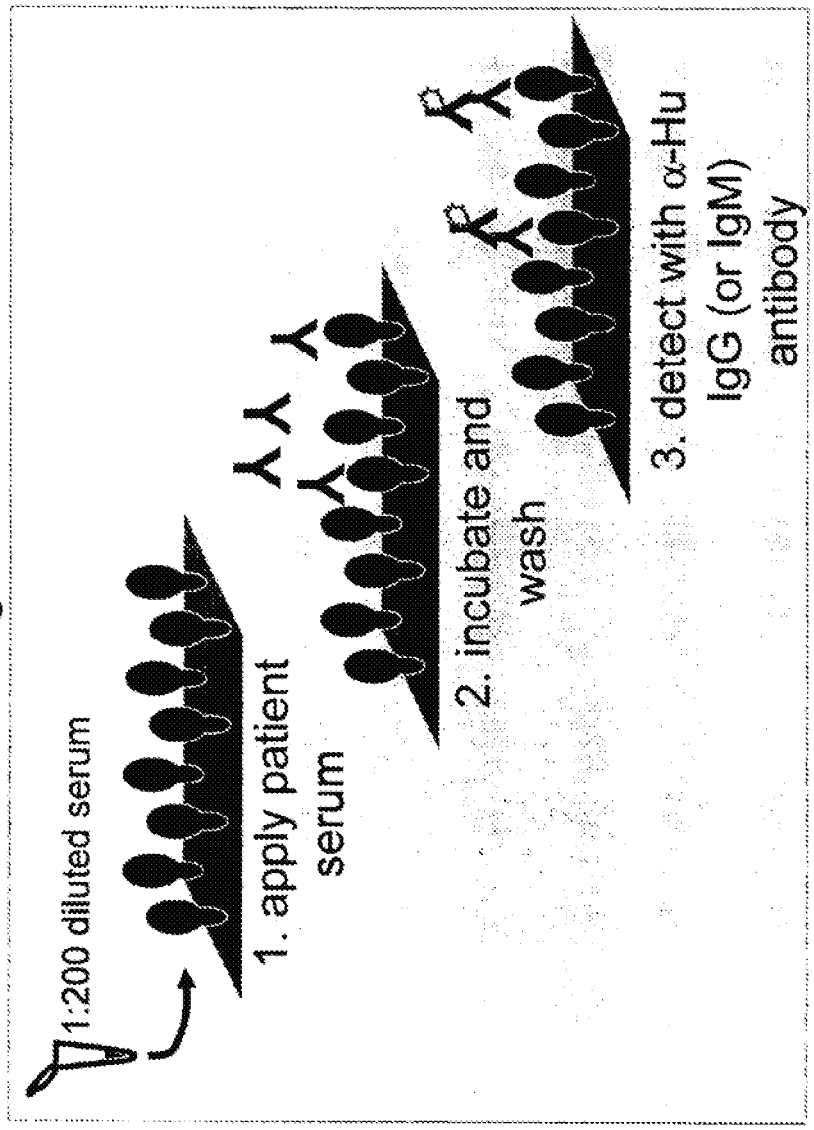
FIG. 3: Assay procedure for detecting auto-antibodies using auto-antigen array.

Binding Serum Auto-Antibodies to Arrays:

Serum samples were applied to the arrays (purchased from Procognia Ltd.; Maidenhead, Berkshire, UK) following clarification (serum had been centrifuged at 10-13K rpm for 2 minutes at 4° C. to remove particulates, including lipids) and dilution 200-fold in 0.1% v/v Triton/0.1% v/v BSA in 1×DPBS with calcium and magnesium (Triton-BSA buffer). Application of each diluted serum (2.5 mL) sample to a separate array was followed by incubation in a Quadriperm dish for 2 hours at room temperature (RT, 20° C.) with gentle orbital shaking (~50 rpm). Arrays were then carefully removed from the Quadriperm dish and any excess probing solution was removed by blotting the sides of the array onto lint-free tissue. Probed arrays were washed twice in fresh Triton-BSA buffer at room temperature for 5 minutes with gentle orbital shaking. The washed slides were then blotted onto lint-free tissue to remove excess wash buffer and were incubated in a secondary staining solution (prepared just prior to use) at room temperature for 2 hours, with gentle orbital shaking and protected from light. The secondary staining solution was a Cy3 labeled rabbit anti-human IgG antibody diluted to the optimal staining concentration in Triton-BSA buffer. The slides were washed three times in Triton-BSA buffer for 5 minutes at RT with gentle orbital shaking, rinsed briefly (5-10 seconds) in distilled water, and centrifuged for 2 minutes at 240×g in a container suitable for centrifugation. To help wick away excess liquid on the arrays, a lint-free tissue was place at the bottom of the arrays during centrifugation. See FIG. 3.

Data Capture:

The probed and dried arrays were then scanned using a microarray scanner capable of using an excitation wavelength of 532 nm, such as the Molecular Devices 4000B microarray scanner, to identify auto-antibodies bound by the array and to determine intensity of auto-antibody binding. The microarray scans produced TIFF images for each array that were used to normalize and score the array data.

Data Normalization:

Raw median signal intensity (also referred to as the relative fluorescent unit, RFU) of each protein feature (also referred to as a spot or antigen) on the array was determined from the TIFF images using GenePix Pro microarray data analysis software. These numerical data were then transferred to Excel where the mean of the raw median signal intensities for each quadruplicate protein feature on the array was determined. All mean data were normalized against the mean for all values below the first quartile of all spots on each array. To this end, a normalization factor for each array was determined by dividing the first quartile value on all the arrays by the first quartile value on each array. Each feature on each array was then multiplied by its respective normalization factor.

Data Scoring:

Once normalized, the data obtained from the scanned arrays were used to score the protein features. A cutoff value for each protein feature on the array was determined by dividing the normalized RFU value on each array by three times the first quartile value for that protein feature on all arrays. The frequency of protein features above three times the cutoff value was determined for each protein feature on each array. The number and intensity of protein features for each sample within and between the stratified disease groups was then determined.

Description of Samples Bound to Arrays:

The serum samples of the normal individuals and individuals diagnosed with SLE that were applied to the arrays were pooled samples from a set of donors having similar characteristics. For instance, all normal samples were pooled and applied to a single array, all the SLE patient serum samples which lacked detectable IFN bioactivity, had an IFN signature, and lacked SSA antibodies were pooled and applied to a single array, all the SLE patient serum samples which had IFN bioactivity, had an IFN signature, and had SSA antibodies were pooled and applied to a single array, and all the SLE patient serum samples which had IFN bioactivity, IFN signature, and no detectable SSA antibodies were pooled and applied to a single array. Table 1 describes the number of patients in each of the normal and SLE pooled sample groups.

TABLE 1

Characteristics of normal and SLE serum samples in respective pools

| | # subjects in pool | IFN bioactivity | IFN signature | SSA |
|---|---|---|---|---|
| Normal samples | 45 | − | N/A | N/A |
| SLE sample 1 | 2 | − | + | − |
| SLE sample 2 | 1 | + | + | + |
| SLE sample 3 | 2 | ++ | + | + |
| SLE sample 4 | 6 | +/++ | + | − |

Figure 4:
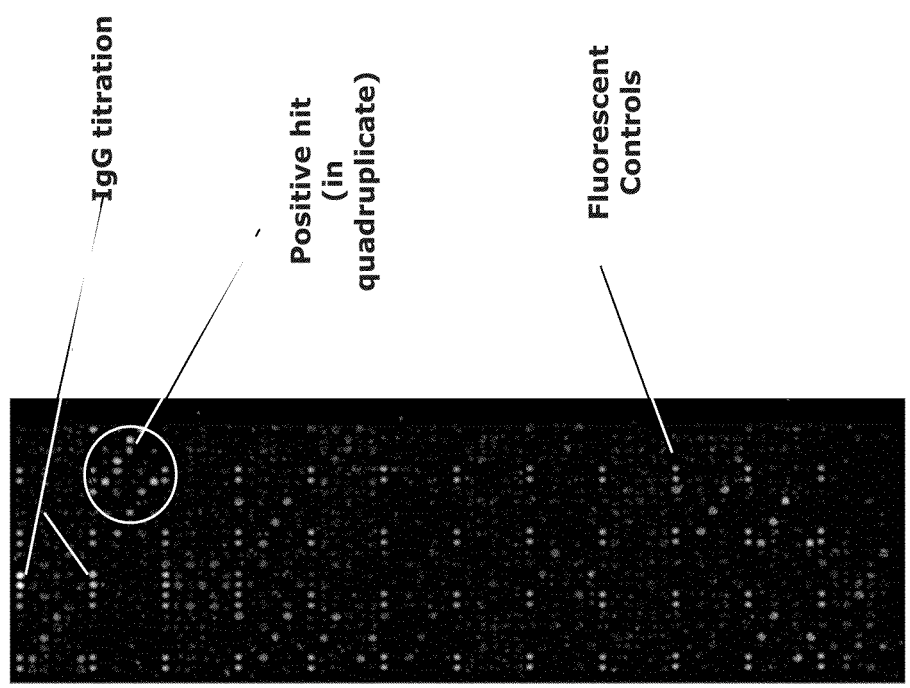
FIG. 4: Auto-antibody array data for auto-antibody detection in normal subjects.
Figure 5:
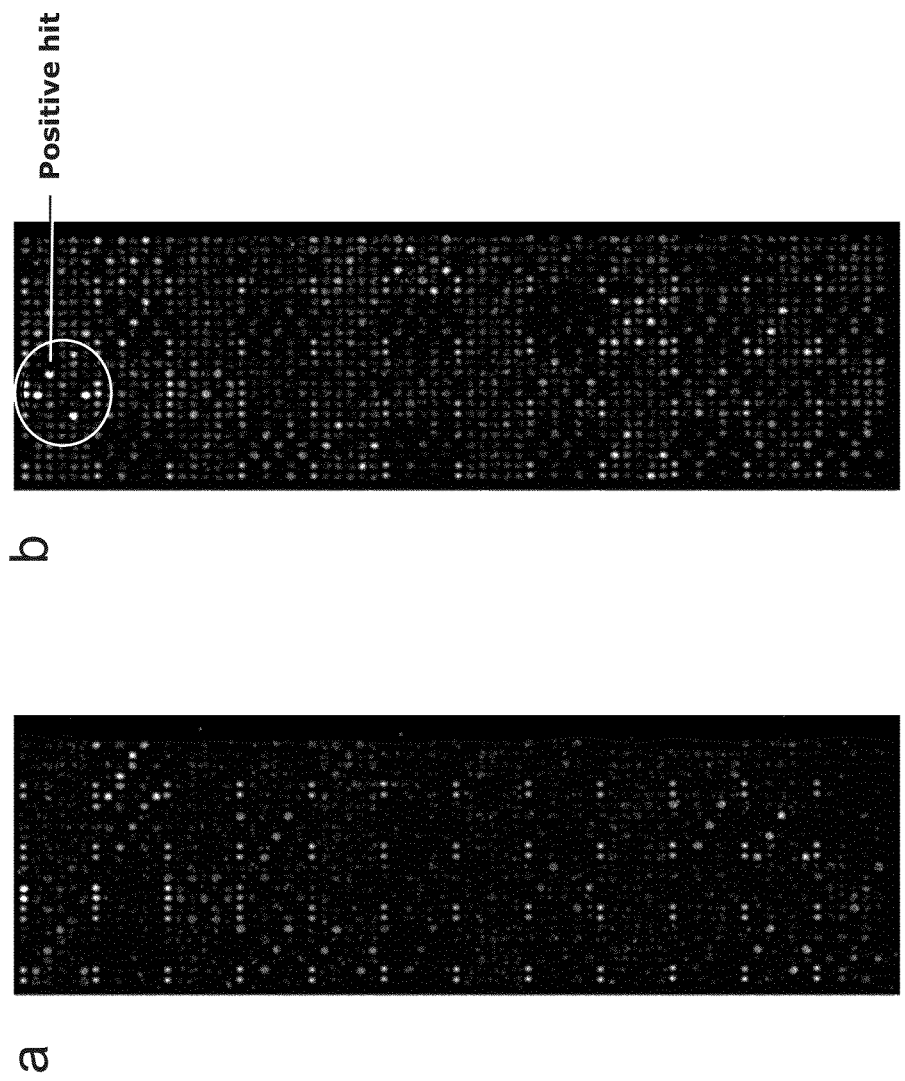
FIGS. 5a and b: Auto-antigen array data for auto-antibody detection in (a) normal subjects and (b) SLE patients having a type I IFN signature but lacking detectable IFN activity.
Figure 6:
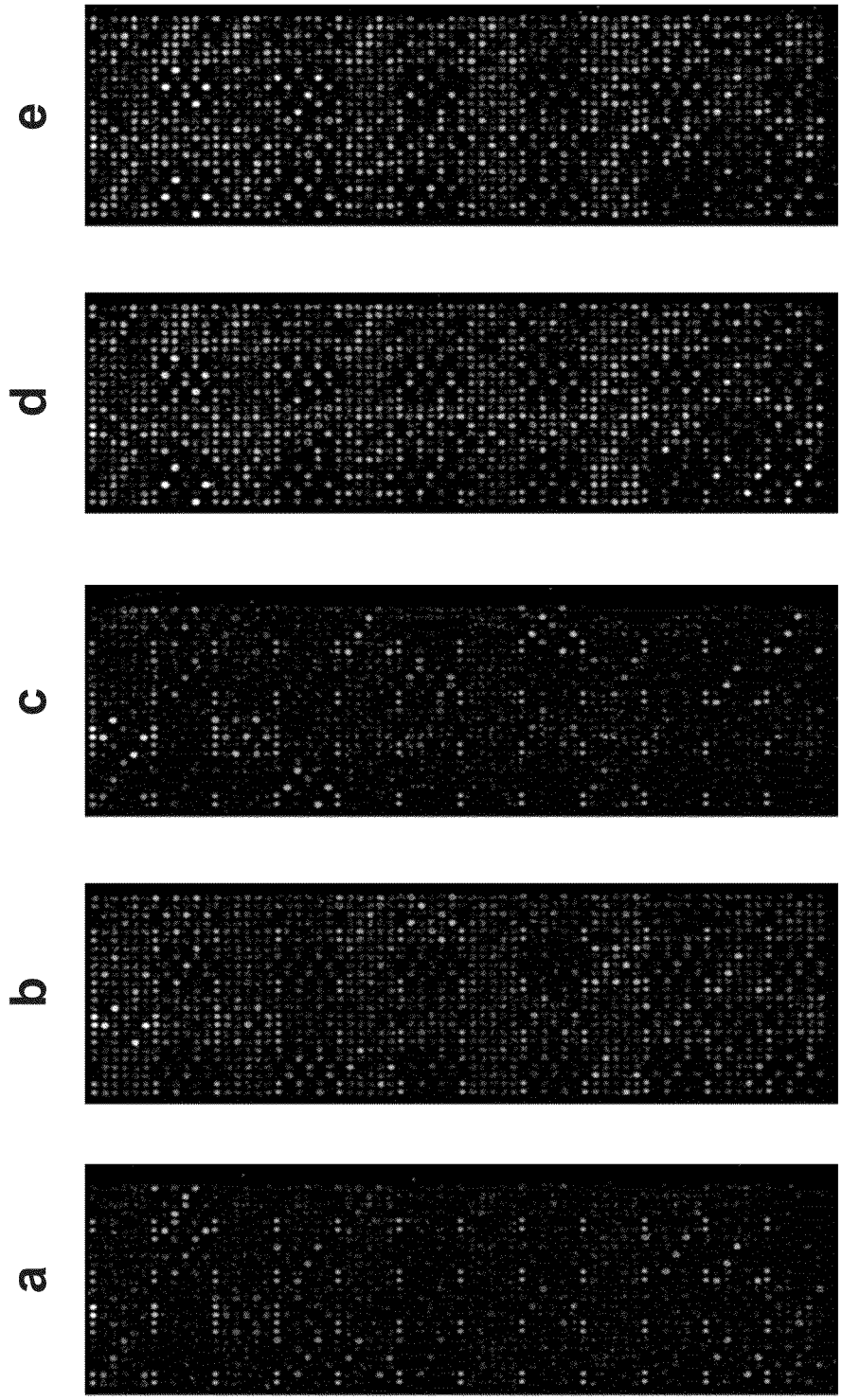
FIG. 6a-e: Auto-antigen array data for auto-antibody detection in (a) normal subjects, (b) SLE patients having a type I IFN signature but lacking detectable IFN activity, (c) SLE patients having a type I IFN signature, detectable IFN activity and detectable Sjogren syndrome antigen A2 (SSA) antibodies, (d) SLE patients having highest type I IFN signature, detectable IFN activity and detectable SSA antibodies, and (e) SLE patients having a type I IFN signature and detectable IFN activity.

Results:

Application of the various pooled samples to the auto-antigen arrays detected a variety of auto-antibodies that were present in the serum of the pooled SLE samples. FIG. 4 shows the detection of auto-antibodies in the pooled normal samples. FIG. 5 provides auto-antibody detection in pooled normal samples (a) and pooled SLE patient samples which lacked detectable IFN activity but exhibited an IFN signature (b). An example of a positive "hit" or protein feature for an auto-antibody in the SLE patient group is highlighted. FIG. 6 provides auto-antigen array data for the normal pooled serum and each of the four different SLE patient groups. The number of auto-antibodies detected by the array for each of the four groups is as follows: 8 in SLE patient group with no detectable IFN activity but with an IFN signature; 11 in SLE patient group with IFN activity, IFN signature, and SSA antibodies; 34 in SLE patient group with greater IFN activity (than the group previously mentioned; see Table 1), IFN signature, and SSA antibodies, and 41 in SLE patients with IFN activity and IFN signature.

Table 2 lists the 49 auto-antigens that were detected as being bound at least 3-fold more by auto-antibodies in the various four different SLE sample pools than in normal pooled sera. Auto-antigens in bold type were detected as being preferentially hound by auto-antibodies in at least 2 of the 4 SLE sample pools. Auto-antigens highlighted in gray were detected as being preferentially bound by auto-antibodies in at least 3 of the 4 SLE sample pools.

TABLE 2

Auto-antigens detected in SLE samples 1, 2, 3, and 4

Acetyl-Coenzyme A acetetyltransferase 2 (acetoacetyl Coenzyme A thiolase)
Adenylosuccinate lyase
S-adenosylhomocysteine hydrolase
Aldolase A, fructose-bisphosphate, transcript variant 1
Ankyrin repeat domain 13
ATP synthase, H+ transporting, mitochondrial F1 complex, beta polypeptide
Cytoskeleton-associated protein 1
Crystallin, alpha B
Cancer/testis antigen 2, transcript variant 2
DNA-damage-inducible transcript 3
Dynein, cytoplasmic, light intermediate polypeptide 2
Down-regulator of transcription 1, TBP-binding (negative cofactor 2)
Eukaryotic translation elongation factor 1 gamma
Exosome component 8
Fas (TNFRSF6) associated factor 1, transcript variant 1
Fumarate hydratase
FIP1 like 1 (S. cerevisiae)
Hypothetical protein FLJ12577
Hook1 protein
Heat shock 90 kDa protein 1, alpha
Heat shock 60 kDa protein 1 (chaperonin)
Heat shock 10 kDa protein 1 (chaperonin 10)
Keratin 14 (epidermolysis bullosa simplex, Dowling-Meara, Koebner)
Keratin 8
Lactate dehydrogenase B
Lin-28 homolog (C. elegans)
Mitogen-activated protein kinase 1, transcript variant 2
Macrophage migration inhibitory factor (glycosylation-inhibiting factor)
MutL homolog 1, colon cancer, nonpolyposis type 2 (E. coli)
Moesin
Peroxisomal D3, D2-enoyl-CoA isomerase TABLE 2-continued Auto-antigens detected in SLE samples 1, 2, 3, and 4

Pleckstrin homology-like domain, family A, member 1
Protein phosphastase 4, regulatory subunit 1
Protein regulator of cytokinesis 1
Preimplantation protein 3, transcript variant 1
Proteasome (prosome macropain) activator subunit 3 (PA28 gamma; Ki)
Pyrroline-5-carboxylate reductase 1, transcript variant 1
Ras-related C3 botulinum toxin substrate 1 (rho family, small GTP binding protein)
Retinoic acid receptor, alpha
RIO kinase 2 (yeast)
Ribosomal protein, large, P1
Sjogren syndrome antigen A2 (60 kDa, ribonucleoprotein autoantigen SS-A/Ro)
Serine/threonine kinase 16
Surfeit 5, transcript variant c
TBC1 domain family, member 2
Tudor and KH domain containing protein
Target of myb1 (chicken)
Tropomyosin 3
Ubiquinol-cytochrome c reductase core protein 1

Example 2

Serum of Individual SLE Patients Confirms Presence and Specificity (for Particular Auto-Antigens) of Auto-Antibodies To further investigate the presence and specificity of auto-antibodies in SLE patients, serum of individual SLE patients was assayed using the auto-antigen arrays. Sera of each of 36 different donors, 11 of which were healthy controls and 25 of which were SLE patients, were separately analyzed on the arrays and processed as described in Example 1. The serum samples obtained from each of the 36 donors were classified according to the presence or absence of IFN bioactivity and IFN signature. The number of donors that shared the same IFN bioactivity and IFN signature characteristics are presented in Table 3.

TABLE 3

Characteristics of individual normal and SLE serum samples

| | # subjects | IFN bioactivity | IFN signature |
|---|---|---|---|
| Normal subjects | 11 | − | N/A |
| SLE Group 1 | 8 | − | − |
| SLE Group 2 | 9 | − | + |
| SLE Group 3 | 8 | + | + |

Application of the serum samples of each of the individual normal donors and SLE patients to the auto-antigen arrays confirmed the presence of auto-antibodies at elevated levels in the serum of SLE patients relative to normal donors. Table 4 provides the 30 most prevalent auto-antibodies present in SLE patients. Some of the auto-antibodies detected by the auto-antigen arrays were present in between 25% and 50% of all SLE patient serum samples.

TABLE 4

Prevalence of auto-antibodies to various antigens in normal and SLE subjects

| Auto-antigen | No. SLE patients w/ auto-Abs | No. normal subjects w/ auto-Abs |
|---|---|---|
| CCAAT/enhancer binding protein (C/EBP), gamma | 3 | 0 |
| DNA-damage-inducible transcript 3 | 3 | 0 |
| Eukaryotic translation elongation factor 1 delta | 3 | 0 |
| Eukaryotic translation elongation factor 1 gamma | 3 | 0 |
| GCN5 general control of amino-acid synthesis 5-like 2 (yeast) | 3 | 0 |
| Homer homolog 2 (*Drosophila*), transcript variant 1 | 3 | 0 |
| Moesin | 3 | 0 |
| Synovial sarcoma, X breakpoint 2, transcript variant 2 | 3 | 0 |
| Ras-related C3 botulinum toxin substrate 1 (rho family, small GTP binding protein) | 4 | 0 |
| Dynein, cytoplasmic, light intermediate polypeptide 2 | 5 | 1 |
| Dom-3 homolog Z (*C. elegans*) | 5 | 0 |
| Heat shock 90 kDa protein 1, alpha | 5 | 0 |
| Lin-28 homolog (*C. clegans*) | 5 | 1 |
| Mitochondrial ribosomal protein L45 | 5 | 0 |
| Preimplantation protein 3, transcript variant 1 | 5 | 0 |
| Spastic paraplegia 20, spartin (Troyer syndrome) | 5 | 1 |
| Tropomyosin 1 (alpha) | 5 | 1 |
| Leucin rich repeat (in FLII) interacting protein 2 | 6 | 1 |
| MutL homolog 1, colon cancer, nonpolyposis type 2 (*E. coli*) | 6 | 1 |
| NudE nuclear distribution gene E homolog 1 (*A. nidulans*) | 6 | 2 |
| NADH dehydrogenase (ubiquinone) 1, alpha/beta subcomplex 1, 8 kDa | 6 | 1 |
| Sjogren syndrome antigen A2 (60 kDa, ribonucleoprotein auto-antigen SS-A/Ro) | 6 | 0 |
| Cytoskeleton-associated protein 1 | 7 | 2 |
| Pleckstrin homology-like domain, family A, member 1 | 7 | 2 |
| Tropomyosin 3 | 7 | 0 |
| Heat shock 10 kDa protein 1 (chaperonin 10) | 8 | 2 |
| Retinoic acid receptor, alpha | 8 | 0 |
| Proteasome (posome, macropain)activator subunit 3 (PA28 gamma; Ki) transc | 9 | 0 |
| Surfeit 5, transcript variant c | 10 | 2 |
| Myxovirus (influenza virus) resistance 1, interferon-inducible protein p78 | 12 | 2 |

Of all the auto-antibodies detected as being present in the serum of individual SLE patients, many were identical to those identified in the pooled SLE patient serum samples described in Example 1. 45 of the 49 auto-antibodies identified in the pooled SLE patient samples (Table 2) were also detected in the serum of the individual SLE patients. Table 5 provides a list of the 45 auto-antibodies that were detected in both the pooled SLE patient serum samples in Example 1 and in the individual SLE patient samples.

TABLE 5

Auto-antibodies detected in both pooled SLE patient serum (Table 2) and individual patients Acetyl-Coenzyme A acetyltransferase 2 (acetoacetyl coenzyme A thioloase)
Adenylosuccinate lyase
S-adenosylhomocysteine hydrolase
Aldolase A, fructose-bisphosphate, transcript variant 1
Ankyrin repeat domain 13
ATP synthase, H+ transporting, mitochondrial F1 complex, beta polypeptide
Cytoskeleton-associated protein 1
Crystallin, alpha B
Cancer/testis antigen 2, transcript variant 2
DNA-damage-inducible transcript 3
Dynein, cytoplasmic, light intermediate polypeptide 2
Down-regulator of transcription 1, TBP-binding (negative cofactor 2)
Eukaryotic translation elongation factor 1 delta
Fas (TNFRSF6) associated factor 1, transcript variant 1
FIP like 1 (*S. cerevisiae*)
Hypothetical protein FLJ12577
Hook1 protein
Heat shock 90 kDa protein1, alpha

TABLE 5-continued

Auto-antibodies detected in both pooled SLE patient serum (Table 2) and individual patients Heat shock 60 kDa protein 1 (chaperonin)
Heat shock 10 kDa protein 1 (chaperonin 10)
Keratin 14 (epidermolysis bullosa simplex, Dowling-meara, Koebner)
Lin-28 homolog (*C. elegans*)
Lactate dehydrogenase B
Mitogen-activated protein kinase 1, transcript variant 2
Macrophage migration inhibitory factor (glycosylation-inhibiting factor)
MutL homolog 1, colon cancer, nonpolyposis type 2 (*E. coli*)
Moesin
Peroxisomal D3, D2-enoyl-CoA isomerase
Pleckstrin homology-like domain, family A, member 1
Protein phosphatase 4, regulatory subunit 1
Protein regulator of cytokinesis 1
Preimplantation protein 3, transcript variant 1
Proteasome (prosome, macropain) activator subunit 3 (AP28 gamma; Ki)
Pyrroline-5-carboxylate reductase 1, transcript variant 1
Ras-related C3 botulinum toxin substrate 1 (rho family, small GTP binding protein)
Retinoic acid receptor, alpha
RIO kinase 2 (yeast)
Sjogren syndrome antigen A2 (60 kDa, ribonucleoprotein autoantigen SS-A/Ro)
Serine/threonine kinase 16
Surfeit 5, transcript variant c
TBC1 domain family, member 2
Tudor and KH domain containing protein
Target of myb1 (chicken)
Tropomyosin 3
Ubiquinol-cytochrome c reductase core protein

Example 3

Serum of SLE Patients Having Both IFN Activity and an IFN Signature have the Most Elevated Number of Auto-Antibodies Examination of the number of auto-antibodies detected on a per patient basis for each of the normal and SLE patients described in Example 2 (Table 3) revealed that serum of SLE patients with both an IFN signature and IFN activity had the greatest number of auto-antibodies detected by the arrays. See Tables 6 and 7. Table 6 presents the number of auto-antibodies detected per patient in each of the three SLE patient groups and the normal patient group described in Example 2.

TABLE 6

Number of auto-antibodies detected per patient according to group

| Normal subjects | IFN activity (−)/ IFN signature (−) | IFN activity (−)/ IFN signature (+) | IFN activity (+)/ IFN signature (+) |
|---|---|---|---|
| 6 | 7 | 11 | 18 |

While serum of SLE patients with IFN activity and an IFN signature had the highest number of per patient auto-antibodies detected by the assay, serum of SLE patients that did not have detectable IFN activity but had an IFN signature had an intermediate number of per patient auto-antibodies, and serum of SLE patients that had no detectable IFN activity or IFN signature had a low number of per patient auto-antibodies.

Table 7 presents the number of autoantibodies detected in at least 10% of SLE patients but not in any, or in nearly none, of healthy donors for each of the three SLE patient groups.

TABLE 7

Relationship of autoantibodies in SLE patient serum to detectable IFN gene signature and activity

| IFN gene signature/ activity | No. autoantibody hits in >10% of SLE patients but negative in healthy donors (n = 25) | No. autoantibody hits in >10% of SLE patients but present in ≤1/25 of healthy donors |
|---|---|---|
| IFN −/− (n = 38) | 4 | 7 |
| IFN +/− (n = 39) | 14 | 27 |
| IFN +/+ (n = 41) | 27 | 42 |
| All SLE (n = 118) | 22 | 34 |

In this assay, serum of SLE patients with IFN activity and an IFN signature had the highest number of auto-antibodies, serum of SLE patients that did not have detectable IFN activity but had an IFN signature had an intermediate number of auto-antibodies, and serum of SLE patients that had no detectable IFN activity or IFN signature had a low number autoantibodies that were not detected in healthy donors (or were detected in only one of twenty five healthy donors) using the criteria shown in Table 7, above.

Autoantibodies against known SLE autoantigens SSA, ribosomal P, and proteosome activator subunit 3 (PA28 g) were detected in SLE patient samples. Autoantibodies against SSA and against ribosomal P, however, were not detected in the particular group of SLE patient samples that lacked both an IFN gene signature and IFN serum activity.

Table 9 lists autoantigens to which the SLE patients had detectable auto-antibodies in an assay performed using the patient samples described in Table 7 (albeit at a later date). Table 9 also provides the percentage of SLE patients (each of all SLE patients, SLE patients having both detectable interferon activity and signature (+/+), detectable interferon activity but not signature (+/−), or nondetectable interferon activity and signature (−/−)), and percentage of normal subjects which had autoantibodies against the various autoantigens.

TABLE 9

Percentage of healthy and SLE subjects having autoantibodies to the indicated autoantigens

| | n = | | | | |
|---|---|---|---|---|---|
| | 25 | 118 | 41 | 39 | 38 |
| | | Total % hits (L, M, H) | | | |
| Name | Normal | All SLE | SLE +/+ | SLE +/− | SLE −/− |
| Ankyrin repeat domain 13 | 0% | 10% | 12% | 10% | 8% |
| ATP synthase, H+ transporting, mitochondrial F1 complex, beta polypeptide | 0% | 10% | 10% | 15% | 5% |
| Chromosome 7 open reading frame 22 | 0% | 8% | 10% | 10% | 3% |
| Hypothetical protein DJ1042K10.2 | 0% | 8% | 10% | 13% | 3% |
| Eukaryotic translation elongation factor 1 gamma | 0% | 9% | 12% | 13% | 3% |
| Fumarate hydratase | 0% | 13% | 24% | 8% | 5% |
| Hepatocellular carcinoma-associated antigen 127 | 0% | 7% | 7% | 3% | 11% |
| Isopentyl-diphosphate delta isomerase | 0% | 8% | 12% | 10% | 3% |
| Macrophage migration inhibitory factor (glycosylation-inhibiting factor) | 0% | 8% | 12% | 8% | 5% |
| Mitochondrial ribosomal protein L45 | 0% | 8% | 7% | 8% | 11% |
| Moesin | 0% | 10% | 15% | 10% | 5% |
| Oxysterol binding protein-like 9, transcript variant 1 | 0% | 14% | 15% | 13% | 13% |
| Protein phosphatase 1, regulatory (inhibitor) subunit 2 pseudogene 9 | 0% | 9% | 12% | 8% | 8% |
| Proteasome (prosome, macropain) activator subunit 3 (PA28 gamma; Ki), transc | 0% | 32% | 46% | 38% | 11% |
| Ras-related C3 botulinum toxin substrate 1 (rho family, small GTP binding protein | 0% | 7% | 12% | 5% | 3% |

TABLE 9-continued

| | | | | | |
|---|---|---|---|---|---|
| RIO kinase 2 (yeast) | 0% | 9% | 12% | 10% | 5% |
| Ribosomal protein, large, P1 | 0% | 12% | 22% | 10% | 3% |
| Sjogren syndrome antigen A2 (60kDA, ribonucleoprotein autoantigen SS-A/Ro) | 0% | 17% | 17% | 26% | 8% |
| Synovial sarcoma, X breakpoint 2, transcript variant 2 | 0% | 11% | 12% | 8% | 13% |
| Serine/threonine kinase 16 | 0% | 12% | 12% | 15% | 8% |
| TBC1 domain family, member 2 | 0% | 10% | 10% | 15% | 5% |
| Tudor and KH domain containing protein | 0% | 12% | 12% | 18% | 5% |
| Target of myb1 (chicken) | 0% | 11% | 12% | 13% | 8% |
| Uridine monophosphate kinase | 0% | 8% | 10% | 10% | 5% |
| Cadherin 19, type 2 | 4% | 11% | 12% | 13% | 8% |
| Cytoskeleton-associated protein 1 | 4% | 17% | 17% | 15% | 18% |
| Crystallin, alpha B | 4% | 16% | 17% | 15% | 16% |
| Cancer/testis antigen 2, transcript variant 2 | 4% | 12% | 12% | 15% | 8% |
| Epidermal growth factor receptor pathway substrate 15 | 4% | 13% | 12% | 18% | 8% |
| Fas (TNFRSF6) associated factor 1, transcript variant 1 | 4% | 8% | 12% | 8% | 5% |
| FIP1 like 1 (*S. cerevisiae*) | 4% | 10% | 10% | 15% | 5% |
| Hook1 protein | 4% | 11% | 12% | 15% | 5% |
| Keratin 8 | 4% | 12% | 12% | 15% | 8% |
| Lactate dehydrogenase B | 4% | 11% | 20% | 8% | 5% |
| Pyrroline-5-carboxylate reductase 1, transcript variant 1 | 4% | 19% | 22% | 21% | 13% |
| Retinoic acid receptor, alpha | 4% | 19% | 29% | 18% | 8% |
| Serologically defined colon cancer antigen 10 | 4% | 9% | 12% | 13% | 3% |
| Tropomyosin 3 | 4% | 17% | 29% | 13% | 8% |

Figure 7:
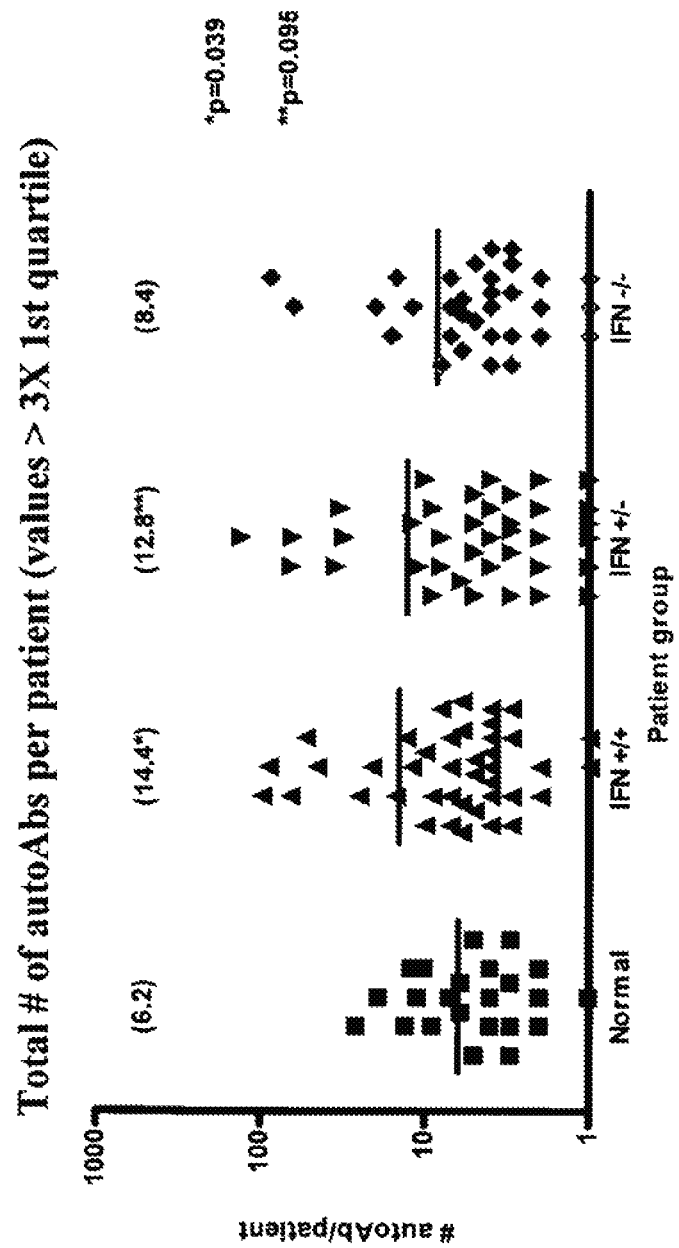
FIG. 7: IFNα serum activity correlates with number of autoantibodies, detected by microarray, per SLE patient.

Correlation of IFNα serum activity with the number of autoantibodies detected per SLE patient or healthy control serum sample is graphically shown in FIG. 7. Total number of autoantibodies per patient or control sample is provided in the graph. Number of autoantibodies was highest in SLE patient serum samples that exhibited both an IFN signature and IFN activity, was next highest in SLE patient serum samples that did not have detectable IFN activity but that did have an IFN signature, was lower in SLE patient serum samples that did not have detectable IFN activity or detectable IFN signature, and was lowest in normal healthy control samples. Autoantibodies were detected using the arrays described in Example 1.

Figure 8:
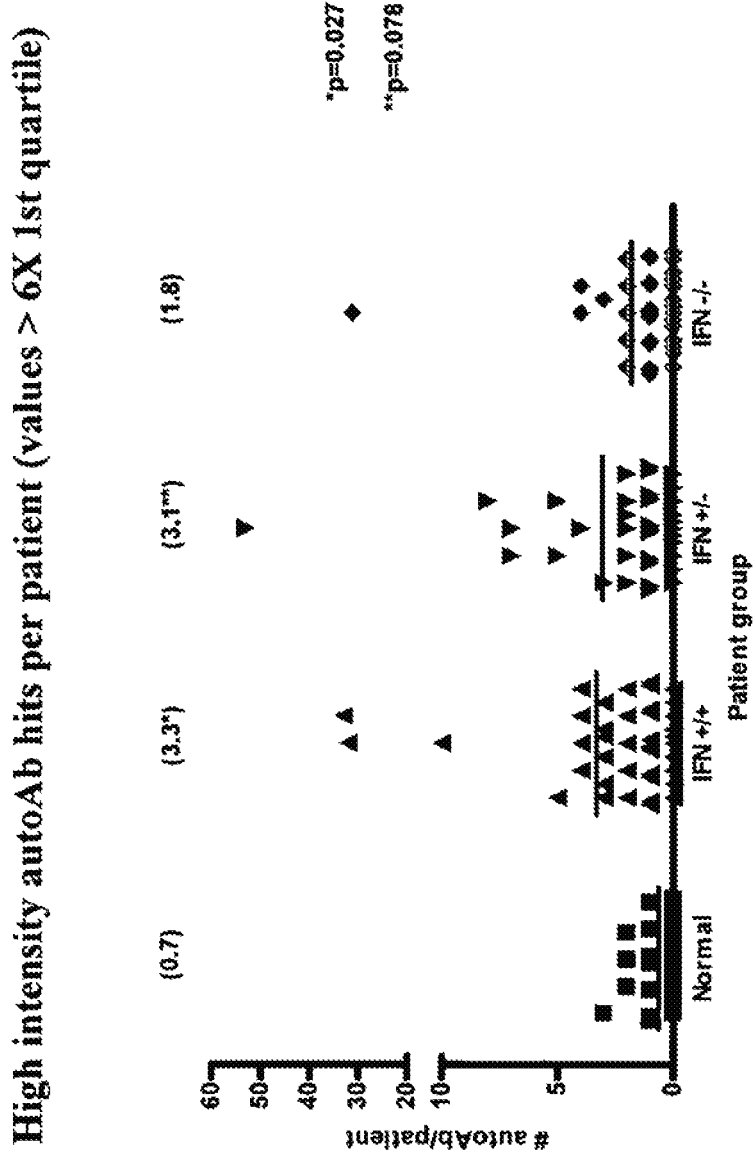
FIG. 8: IFNα serum activity correlates with intensity of autoantibodies, detected by microarray, per SLE patient.

A graphical representation of the correlation of IFNα serum activity with the intensity of autoantibodies detected per SLE patient or healthy control serum sample is shown in FIG. 8. Autoantibodies were detected using the arrays described in Example 1. Similar to the number of autoantibodies, intensity of autoantibodies was highest in SLE patient serum samples that exhibited both an IFN signature and IFN activity, was next highest in SLE patient serum samples that did not have detectable IFN activity but that did have an IFN signature, was lower in SLE patient serum samples that did not have detectable IFN activity or detectable IFN signature, and was lowest in normal healthy control samples.

Figure 9:
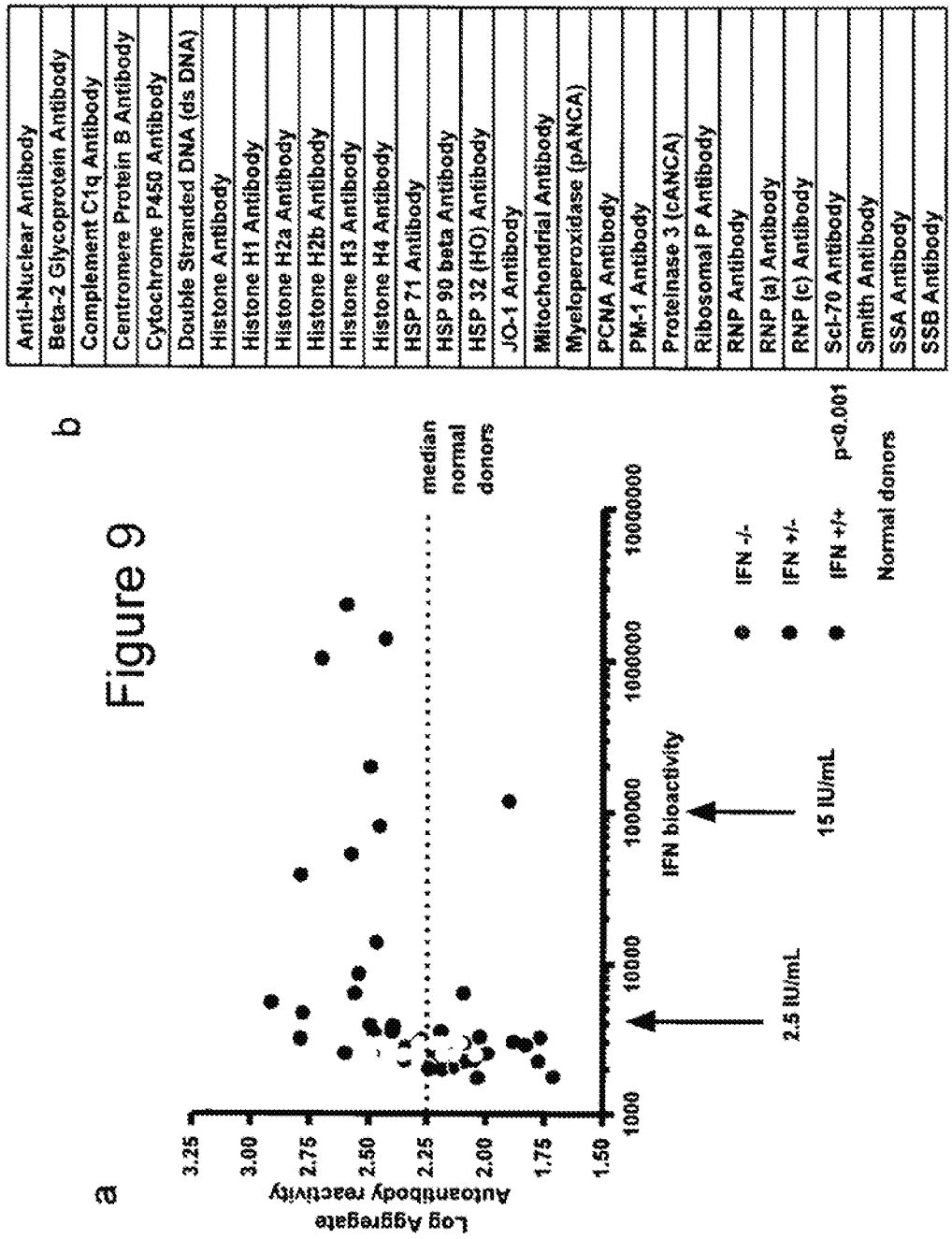

The correlation of IFNα serum activity with autoantibody number and intensity observed in the array assays described in Example 1 were validated by Luminex assay. Luminex assays were outsourced to and conducted by rules based medicine (world wide web at rulesbasedmedicine.com). FIG. 9a provides a graphical representation of the results obtained from the assay. The Luminex assay confirmed that the number/intensity of autoantibodies was highest in SLE patient serum samples that exhibited both an IFN signature and IFN activity, was next highest in SLE patient serum samples that did not have detectable IFN activity but that did have an IFN signature, and was lowest in SLE patient serum samples that did not have detectable IFN activity or signature and in normal healthy control samples. FIG. 9b provides a list of the autoantibodies that were screened for in the Luminex assay.

Figure 10:
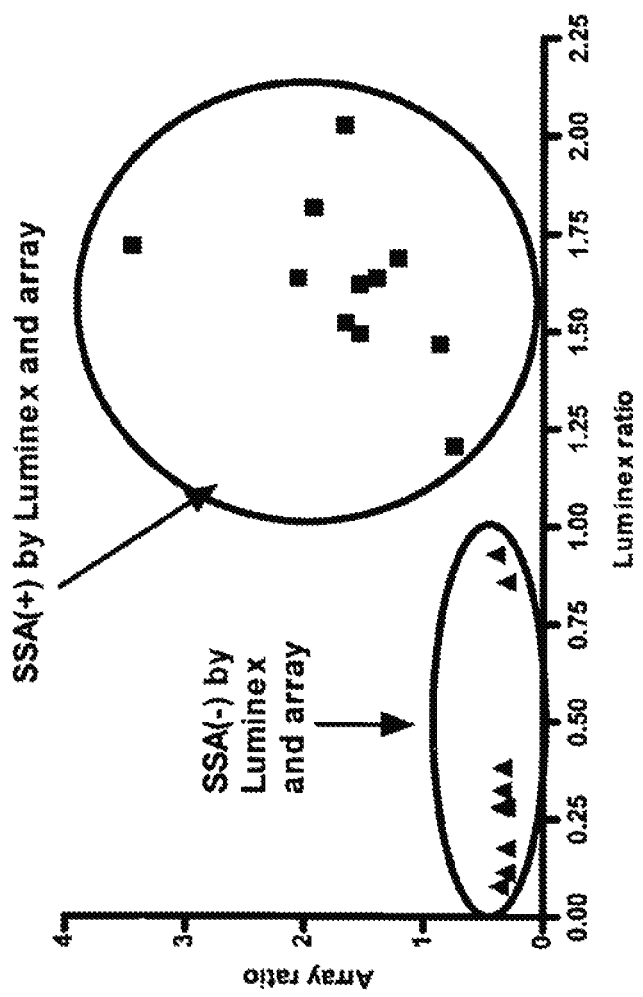
FIG. 10: Confirmation of anti-SSA antibody detection by Luminex. Both Luminex and microarray assays identically classified the presence of SSA antibodies in 20 of 20 SLE samples.

The presence of SSA autoantibodies in certain SLE patient serum samples was also validated by the Luminex assay. As FIG. 10 shows, all 20 SLE patient serum samples that were tested by both the arrays discussed in Example 1 and by the Luminex assay were classified identically for the presence of SSA autoantibodies.

Example 4

Presence of Autoantibodies Against Retinoic Acid Receptors in SLE Patients

IgG class autoantibodies against retinoic acid receptor alpha (RARα) were identified in a high percentage of SLE samples. Presence of RARα autoantibodies also correlated well with presence of IFN gene signature and/or IFN bioactivity in the SLE patient serum samples. See Table 8.

TABLE 8

Prevalence of RARα autoantibodies in SLE patient serum samples according to IFN gene signature and IFN activity

| | Patient group (IFN gene signature/activity) | | | |
|---|---|---|---|---|
| | SLE IFN (−/−) | SLE IFN (+/−) | SLE IFN (+/+) | All SLE |
| % samples with RARα autoantibodies | 8 | 18 | 29 | 19 |

Individual SLE patient samples were next tested by ELISA assay to determine whether the RARα autoantibodies bound to full length RARα (a 462 amino acid protein) or to the ligand binding domain of RARα (amino acid residues 176-462).

Briefly, to carry out the ELISA, MaxiSorp ELISA plates were coated with 100 uL recombinant human full-length RARα or its ligand binding domain prepared at 1 ug/mL in phosphate buffered saline overnight at 2-8° C. Following the overnight incubation, plates were washed 4 times using PBS/ 0.1% tween 20 wash buffer and then tapped on paper towels to remove residual liquid from the wells. The washed plates were blocked with 300 µL of 1% casein and incubated at RT for 1 hour. Following blocking, the plates were again washed 4 times using PBS/0.1% tween 20 wash buffer and then tapped on paper towels to remove residual liquid from the wells. After this wash step, pooled or individual human sera (SLE and normal sera) were serially diluted from 1:100 to 1:400 in assay buffer. One hundred microliters of serum sample diluted in assay buffer was added to the wells of the assay plates and incubated for 1 hr at RT with shaking at 600 rpm. Following incubation of the serum samples with the coated wells, the plates were washed 4 times using PBS/0.1% tween 20 wash buffer and were tapped on paper towels to remove any residual liquid from the wells. One hundred microliters of goat anti-human IgG Fc specific-HRP (Jackson, P/N 109-035-098) at 1:40K in Assay Buffer OR donkey anti-goat IgG (H+L)-HRP (Jackson, P/N 705-035-147) at 1:30K in Assay Buffer were added to each well of the assay plates and incubated for 1 hr at RT, with shaking at 600 rpm. Following this incubation, plates were washed 4 times using PBS/0.1% tween 20 wash buffer and then tapped on paper towels to remove residual liquid from the wells. One hundred microliters of TMB substrate was added to each well and the plates were incubated for 10 minutes at RT. One hundred microliters of stop solution was then added to the wells. Absorbance was then determined at 450 nm using a Molecular Devices SpectraMax plate reader. Resultant optical densities from SLE subjects were compared to those generated from normal healthy donors to identify subjects possessing autoantibodies reactivity against full-length RARα or its ligand binding domain.

Figure 11:
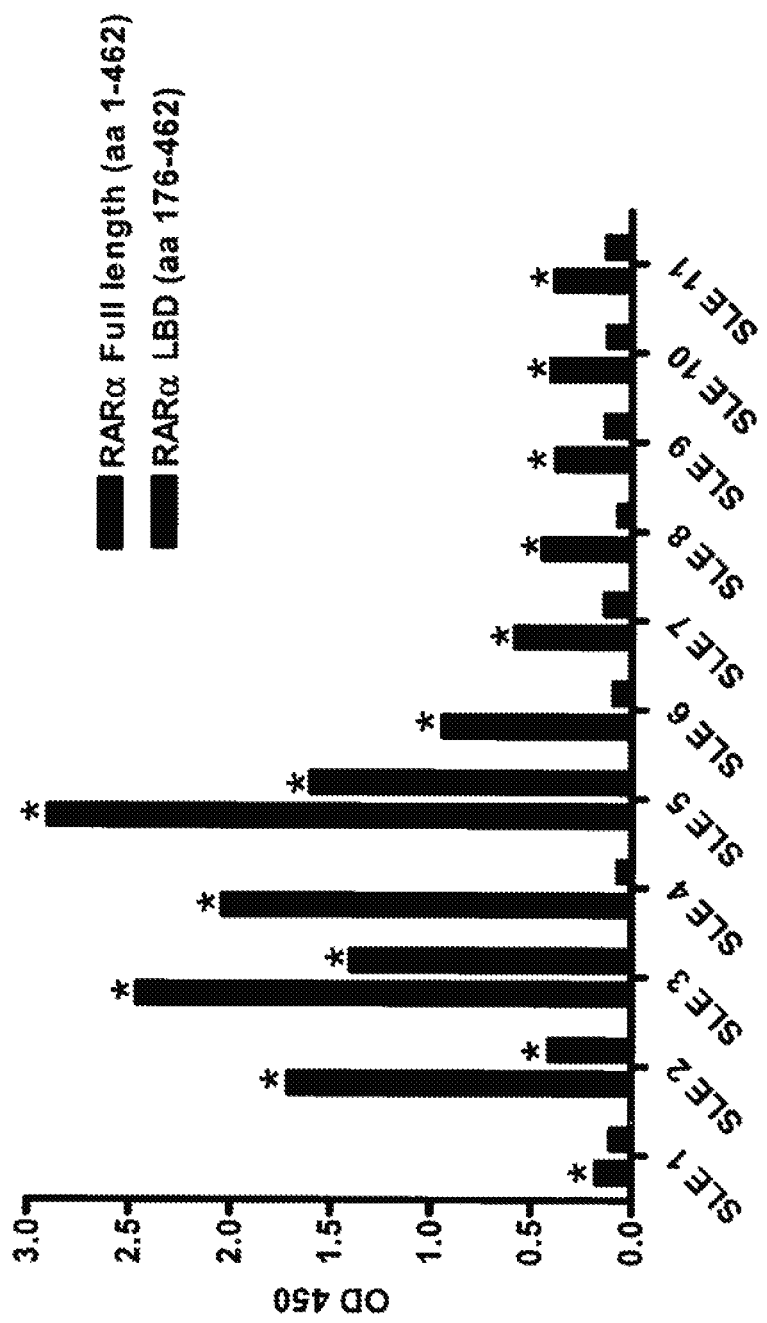
FIG. 11: RARα autoantibodies are reactive against multiple domains of the RARα protein.

FIG. 11 shows that the RARα autoantibodies were reactive against multiple domains of the protein. For example, significant levels of autoantibodies against the ligand binding domain of RARα (amino acid residues 176-462), were detected in serum of several SLE patients, e.g., patients 3 and 5; even higher levels of RARα autoantibody against the full-length RARα protein were detected in these same patients.

The retinoic acid and retinoid X receptors are a (RA(X)R) family of ligand-activated nuclear transcription factors that include RARα, RARβ, RARγ, RXRα, RXRβ, RXRγ, and their isoforms. To determine whether other autoantibodies against other RA(X)R family members are present in SLE patient serum samples, ELISA assays were conducted to detect autoantibodies against RARα, RARβ, RARγ, RXRα, and RXRβ in each of eight different SLE patient serum samples. These ELISA assays were performed similarly to those described immediately above, except the wells of the ELISA plates were coated with RARα, RARβ, RARγ, RXRα, or RXRβ in place of RARα or its ligand binding domain.

FIG. 12 shows the results of the ELISA assays. At least one autoantibody against an RA(X)R family member was significantly elevated in each SLE patient serum sample relative to the healthy control serum sample, verifying the prevalence of autoantibodies against RA(X)R family members in serum of SLE patients.

We claim:

1. A method of treating a patient having lupus comprising:
    administering an effective amount of an antibody that binds to and decreases or inhibits type I IFN or IFNα activity;
    wherein the patient having lupus comprises autoantibodies that bind at least any three or more auto-antigens of:
    (a) Myxovirus (influenza virus) resistance 1, interferon-inducible protein p78;
    (b) surfeit 5, transcript variant c;
    (c) proteasome (posome, macropain) activator subunit 3 (PA28 gamma; Ki) transc;
    (d) retinoic acid receptor, alpha;
    (e) Heat shock 10 kDa protein 1 (chaperonin 10);
    (f) Tropomyosin 3;
    (g) Pleckstrin homology-like domain, family A, member 1;
    (h) Cytoskeleton-associated protein 1;
    (i) Sjogren syndrome antigen A2 (60 kDa, ribonucleoprotein auto-antigen SS-A/Ro);
    (j) NADH dehydrogenase (ubiquinone) 1, alpha/beta subcomplex 1, 8 kDa;
    (k) NudE nuclear distribution gene E homolog 1 (*A. nidulans*);
    (l) MutL homolog 1, colon cancer, nonpolyposis type 2 (*E. coli*);
    (m) leucine rich repeat (in FLII) interacting protein 2;
    (n) tropomyosin 1 (alpha);
    (o) spastic paraplegia 20, spartin (Troyer syndrome);
    (p) preimplantation protein, transcript variant 1;
    (q) mitochondrial ribosomal protein L45; and
    (r) fumarate hydratase and
    wherein the agent reduces the number or levels of the auto-antibodies that bind at least any three auto-antigens in the patient.

2. The method of claim 1 further comprising detecting reduction of the number or levels of the auto-antibodies that bind the at least any three auto-antigens in the patient.

3. The method of claim 1 wherein the patient exhibits a type I IFN or IFNα-inducible pharmacodynamic (PD) marker expression profile, said profile comprising up-regulated expression or activity of genes MX1, LY6E, IFI27, OAS1, IFIT1, IFI6, IFI44L, ISG15, LAMP3, OASL, RSAD2, and IFI44.

4. The method of claim 1 wherein the antibody is MEDI-545.

5. The method of claim 1 wherein the antibody is specific for one or more type I IFNs, but is not MEDI-545.

6. The method of claim 1 wherein administering the antibody alleviates one or more symptoms of lupus.

7. The method of claim 1 wherein the antibody is administered at a dose between approximately 0.03 and 30 mg/kg.

8. The method of claim 7 wherein the antibody is administered at a dose between 0.03 and 3.0 mg/kg.

9. The method of claim 8 wherein the antibody is administered at a dose between 0.03 and 1 mg/kg.

10. The method of any one of claims 7-9 wherein the levels of the auto-antibodies are reduced at least 10%.

11. The method of claim 10 wherein levels of the auto-antibodies are reduced at least 20%.

12. The method of claim 10 wherein the levels of the auto-antibodies are reduced at least 30%.

13. The method of claim 10 wherein levels of the auto-antibodies are reduced at least 50%.

14. The method of claim 1 wherein the lupus is mediated by upregulated expression or activity of at least IFN subtypes 1, 2, 8, and 14.

15. The method of claim 1 wherein the patient exhibits a type I IFN or IFNα-inducible pharmacodynamic (PD) marker expression profile comprising up-regulated expression or activity of genes IFI27, IFI6, IFI44L, RSAD2, and IFI44.

* * * * *